US011116728B2

(12) United States Patent
Friesen et al.

(10) Patent No.: US 11,116,728 B2
(45) Date of Patent: *Sep. 14, 2021

(54) MULTIPARTICULATES OF SPRAY-COATED DRUG AND POLYMER ON A MELTABLE CORE

(71) Applicant: Bend Research, Inc., Bend, OR (US)

(72) Inventors: Dwayne Thomas Friesen, Bend, OR (US); Leah E. Appel, Bend, OR (US); Joshua Richard Shockey, Bend, OR (US); Sanjay Konagurthu, Bend, OR (US); Edward Dennis LaChapelle, Bend, OR (US)

(73) Assignee: Bend Research, Inc., Bend, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/440,907

(22) Filed: Jun. 13, 2019

(65) Prior Publication Data

US 2019/0307702 A1 Oct. 10, 2019

Related U.S. Application Data

(63) Continuation of application No. 12/312,826, filed as application No. PCT/IB2007/003612 on Nov. 19, 2007, now Pat. No. 10,357,462.

(60) Provisional application No. 60/867,898, filed on Nov. 30, 2006.

(51) Int. Cl.
*A61K 9/50* (2006.01)

(52) U.S. Cl.
CPC .......... *A61K 9/5078* (2013.01); *A61K 9/5042* (2013.01); *A61K 9/5047* (2013.01); *A61K 9/5084* (2013.01)

(58) Field of Classification Search
CPC .. A61K 9/5078; A61K 9/5042; A61K 9/5047; A61K 9/5084
USPC ....................................................... 424/484
See application file for complete search history.

(56) References Cited

U.S. PATENT DOCUMENTS

| | | | |
|---|---|---|---|
| 4,871,549 A | 10/1989 | Ueda et al. | |
| 4,897,270 A | 1/1990 | Deutsch et al. | |
| 5,082,669 A | 1/1992 | Shirai et al. | |
| 5,190,760 A | 3/1993 | Baker | |
| 5,229,135 A | 7/1993 | Philippon et al. | |
| 5,270,055 A | 12/1993 | Moest | |
| 5,336,433 A | 8/1994 | Lagnemo et al. | |
| 5,376,384 A | 12/1994 | Eichel et al. | |
| 5,478,573 A | 12/1995 | Eichel et al. | |
| 5,536,507 A | 7/1996 | Abramowitz et al. | |
| 5,580,578 A | 12/1996 | Oshlack et al. | |
| 5,593,690 A | 1/1997 | Akiyama et al. | |
| 5,607,697 A | 3/1997 | Alkire et al. | |
| 5,639,476 A | 6/1997 | Oshlack et al. | |
| 5,656,291 A | 8/1997 | Olsson et al. | |
| 5,733,575 A | 3/1998 | Mehra et al. | |
| 5,834,024 A | 11/1998 | Heinicke et al. | |
| 5,840,329 A | 11/1998 | Bai | |
| 5,914,134 A | 6/1999 | Sharma | |
| 5,952,005 A | 9/1999 | Olsson et al. | |
| 6,013,282 A | 1/2000 | Mehra et al. | |
| 6,027,748 A | 2/2000 | Conte et al. | |
| 6,033,687 A | 3/2000 | Heinicke et al. | |
| 6,039,976 A | 3/2000 | Mehra et al. | |
| 6,068,859 A | 5/2000 | Curatolo et al. | |
| 6,077,544 A | 6/2000 | Debregeas et al. | |
| 6,086,920 A | 7/2000 | Frisbee et al. | |
| 6,117,452 A | 9/2000 | Ahlgren et al. | |
| 6,194,000 B1 | 2/2001 | Smith et al. | |
| 6,214,385 B1 | 4/2001 | Heinicke et al. | |
| 6,228,400 B1 | 5/2001 | Lee et al. | |
| 6,270,805 B1 | 8/2001 | Chen et al. | |
| 6,346,269 B1 | 2/2002 | Hsiao et al. | |
| 6,723,358 B1 | 4/2004 | Van Lengerich et al. | |
| 2001/0055619 A1 | 12/2001 | Petereit et al. | |
| 2002/0068084 A1 | 6/2002 | Staniforth | |
| 2003/0099700 A1 | 5/2003 | Faham et al. | |
| 2004/0013734 A1 | 1/2004 | Babcock et al. | |
| 2004/0026546 A1 | 2/2004 | Czekai et al. | |
| 2005/0123627 A1 | 6/2005 | Hagen et al. | |
| 2005/0186285 A1 | 8/2005 | Ray et al. | |
| 2006/0127478 A1 | 6/2006 | Zerbe et al. | |

(Continued)

FOREIGN PATENT DOCUMENTS

| | | |
|---|---|---|
| CA | 2229650 | 8/2006 |
| EP | 0169105 | 8/1991 |
| EP | 0309051 | 3/1992 |

(Continued)

OTHER PUBLICATIONS

Fan, Y.Y. et al., "An Investigation of Pulsatile Release Tablets with Ethyicellulose and Eudragit L as Film Coating Materials and Cross-Liked Polyvinylpyrrolidone in the Core Tablets," *Journal of Controlled Release*, vol. 77, Issue 3, pp. 245-251 (Dec. 2001).

International Search Report for PCT/IB2007/003612 (dated Apr. 16, 2008).

Reo, J.P. et al,, "Taste Masking Science and Technology Applied to Compacted Oral Solid Dosage Forms—Part 3," *American Pharmaceutical Review*, vol. 5, No. 2, pp. 8-13 (Sep. 2002).

Shirai, Y. et al., "A Novel Fine Granule System for Masking Bitter Taste," *Biol. Pharm. Bull.*, vol. 16, No. 2, pp. 172-177 (Feb. 1993).

(Continued)

*Primary Examiner* — Adam C Milligan
(74) *Attorney, Agent, or Firm* — Klarquist Sparkman, LLP

(57) ABSTRACT

A pharmaceutical composition comprises multiparticulates comprising a melt-congeal core and a solid amorphous dispersion layer of a poorly water soluble drug and polymer. The multiparticulates are suitable for improving bioavailability of poorly water soluble drugs. The melt-congeal cores facilitate application of the solid amorphous dispersion layer, and allow incorporation of additional optional components to the core so as to adjust the release of drug from the multiparticulate.

11 Claims, 1 Drawing Sheet

(56) References Cited

U.S. PATENT DOCUMENTS

2010/0068276 A1 3/2010 Friesen et al.

FOREIGN PATENT DOCUMENTS

| EP | 0409254 | 3/1993 |
|---|---|---|
| EP | 0523847 | 4/1996 |
| EP | 0737473 | 10/1996 |
| EP | 0494972 | 11/1996 |
| EP | 1027886 | 8/2000 |
| EP | 1356808 | 10/2003 |
| EP | 2091519 | 6/2015 |
| WO | WO93/00991 | 1/1993 |
| WO | WO94/01093 | 1/1994 |
| WO | WO95/03765 | 2/1995 |
| WO | WO95/03785 | 2/1995 |
| WO | WO01/036698 | 1/2001 |
| WO | WO01/52813 | 7/2001 |
| WO | WO01/80826 | 11/2001 |
| WO | WO2005/053651 | 6/2005 |
| WO | WO2006/082500 | 8/2006 |
| WO | WO2006/102964 | 10/2006 |
| WO | WO2008/065504 | 6/2008 |

OTHER PUBLICATIONS

Sun, Y. et al., "Pharmaceutical Approaches of Taste Masking in Solid Dosage Forms," *American Pharmaceutical Review*, pp. 16-28 (1999).

Office Action for European Application No. 07825725.0 (dated Jan. 18, 2010).

Office Action for European Application No. 07825725.0 (dated Dec. 13, 2011).

Office Action for European Application No. 07825725.0 (dated Oct. 23, 2013).

Written Opinion for PCT/IB2007/003612 (dated May 30, 2009).

MULTIPARTICULATES OF SPRAY-COATED DRUG AND POLYMER ON A MELTABLE CORE

CROSS REFERENCE TO RELATED APPLICATIONS

This is a Continuation of U.S. patent application Ser. No. 12/312,826, filed May 28, 2009, which is a 371 of International Application No. PCT/IB2007/003612, filed Nov. 19, 2007, which was published in English under PCT Article 21(2), which claims the benefit of U.S. Provisional Patent Application No. 60/867,898, filed Nov. 30, 2006, all of which are hereby incorporated by reference

BACKGROUND OF THE INVENTION

The present invention relates to a pharmaceutical composition comprising a drug and polymer spray-coated onto a meltable core.

It is well known that poorly water soluble drugs may be formulated as a solid amorphous dispersion of a drug in a polymer to improve the bioavailability of poorly soluble drugs. Preferred solid amorphous dispersions are formed by spray drying. Such solid amorphous dispersions are also referred to as molecular dispersions. A drawback of such spray dried dispersions is that the particles resulting from the spray-drying process are often very small (typically less than 100 microns in diameter) and have high specific volume (typically greater than 3 cm$^3$/g). These properties make spray dried dispersions difficult to handle, and therefore complicate formulation of such dispersions into dosage forms suitable for oral delivery.

One approach to increasing the size and density of such solid amorphous dispersions is to spray-coat the drug and polymer onto an inert core. For example, the drug and polymer may be spray-coated onto an inert sugar sphere or microcrystalline cellulose. See, e.g., WO 02/38126. However, spray-coating such materials presents several problems. First, conventional sugar cores and the like are friable. Such materials have a tendency to break apart into smaller pieces in the fluid bed during the coating process. The fine material can be swept up into the gas stream, resulting in an inefficient coating process. In addition, the average core size tends to decrease as the coating time increases, resulting in a size distribution that changes over time. Since the release rate of the drug is dependent on the surface area of the multiparticulate, the dissolution rate of the spray-coated multiparticulates will be a function of the coating time. This can lead to non-reproducible dissolution rates from spray-coated multiparticulates due to slight differences in coating conditions from batch to batch. Conventional sugar cores and the like also tend to have rough, irregular surfaces, which can be difficult to coat uniformly.

Another problem associated with spray-coating on to conventional excipients is that the drug dissolution rate from such multiparticulates can be slow. Dissolution rate is dependent on the size of the multiparticulate and composition of the amorphous dispersion layer. It is desired to form small cores to coat, since smaller multiparticulates generally have higher dissolution rates. However, conventional sugar cores and the like are difficult to obtain in small sizes. In addition, surface irregularities tend to increase as the size of these particles decrease, making uniform coating difficult.

Another problem associated with sugar cores is that the sugar can act as an osmogen. When the particle is administered to an aqueous use environment, the particle can absorb water. The sugar core may rapidly absorb water, causing the multiparticule to rupture and prematurely release the drug.

What is therefore desired is a composition comprising a solid amorphous dispersion of drug and polymer coated onto a small, smooth inert core to provide a multiparticulate that has a size and density that facilitates processing of the dispersion into oral dosage forms, and that also allows the drug dissolution rate and release rate of the drug to be adjusted.

BRIEF SUMMARY OF THE INVENTION

In a first aspect, a pharmaceutical composition comprises multiparticulates. The multiparticulates comprise a melt-congeal core surrounded by a solid amorphous dispersion layer comprising a drug and a polymer, wherein at least a major portion of the drug in the solid amorphous dispersion layer is amorphous and wherein at least a portion of the solid amorphous dispersion layer is in the form of a solid solution. The melt-congeal core comprises a matrix material present in an amount of at least 30 wt % of the core. The matrix material is solid at 25° C. The matrix material has a melt temperature of less than 200° C. The matrix material is selected from the group consisting of waxes, long chain alcohols ($C_{12}$ or greater), fatty add esters, glycolized fatty acid esters, phosphoglycerides, polyoxyethylene alkyl ethers, long chain carboxylic acids ($C_{12}$ or greater), sugar alcohols, and mixtures thereof.

Preferably, the matrix material is selected from the group consisting of fatty acids esters, waxes, long-chain alcohols, ethoxylated fatty acid esters, long-chain carboxylic acids, and mixtures thereof.

Preferred fatty acid esters are glyceryl behenate and hydrogenated cottonseed oil.

Preferred waxes include microcrystalline wax, paraffin, ceresin wax and carnuaba wax.

Preferred long-chain alcohols include cetostearyl alcohol, stearyl alcohol and cetyl alcohol.

Preferred ethoxylated fatty acid esters include polyoxyl stearates and polyoxyl behenates.

In one embodiment, the matrix material is hydrophobic and poorly water soluble. Exemplary matrix materials that are hydrophobic include waxes and fatty acid esters.

In another embodiment, the matrix material is selected from the group consisting of fatty acids esters, waxes, long-chain alcohols, ethoxylated fatty acid esters, long-chain carboxylic acids, and mixtures thereof, and the polymer is selected from the group consisting of hydroxypropyl methyl cellulose, polyvinylpyrrolidone, hydroxypropyl methyl cellulose acetate succinate, cellulose acetate phthalate, cellulose acetate trimellitate, and carboxymethyl ethyl cellulose.

In another embodiment, the matrix material is selected from the group consisting of fatty acids esters, waxes, long-chain alcohols, ethoxylated fatty acid esters, long-chain carboxylic acids, and mixtures thereof, and the polymer is selected from the group consisting of hydroxypropyl methyl cellulose, and hydroxypropyl methyl cellulose acetate succinate.

In another embodiment, the polymer is hydroxypropyl methyl cellulose acetate succinate.

In another embodiment, the core further comprises a swelling agent, the swelling agent being capable of imbibing fluid and swelling so as to rupture the core.

In another embodiment, the core further comprises the drug.

In another embodiment, the core further comprises a second drug.

In another embodiment, the core further comprises a dissolution enhancer.

In another embodiment, the core comprises a dissolution-inhibiting agent.

In another embodiment, the multiparticulates comprise an exterior coating surrounding the solid amorphous dispersion layer.

In another aspect of the invention, a process for making a pharmaceutical composition of multiparticulates comprises the steps:
(a) forming a molten mixture comprising at least 30 wt % of a matrix material, the matrix material being selected from the group consisting of waxes, long chain alcohols ($C_{12}$ or greater), fatty acid esters, glycolized fatty acid esters, phosphoglycerides, polyoxyethylene alkyl ethers, long chain carboxylic acids ($C_{12}$ or greater), sugar alcohols, and mixtures thereof;
(b) atomizing the molten mixture of step (a) to form droplets;
(c) congealing the droplets of step (b) to form solid cores;
(d) forming a spray solution comprising a solvent, a poorly water soluble drug and a polymer; and
(e) spray-coating the spray solution onto the cores of step (c) to form a solid amorphous dispersion layer comprising the poorly water soluble drug and the polymer surrounding the core, wherein at least a major portion of the drug in the solid amorphous dispersion layer is amorphous and wherein at least a portion of the solid amorphous dispersion layer is in the form of a solid solution.

By "multiparticulates" is meant a plurality of small particles having a volume-weighted mean diameter of from about 10 microns up to about 3 mm. Unless otherwise noted, the size of the multiparticulates refers to the diameter of the core and surrounding solid amorphous dispersion layer, but excludes any optional exterior coating applied over the solid amorphous dispersion layer. The multiparticulates preferably have an average diameter of less than 500 microns, and more preferably less than about 300 microns.

The use of a spray-coated solid amorphous dispersion on a melt-congeal core provides a number of advantages. First, the melt-congeal cores are less friable than conventional sugar cores. The melt-congeal cores do not break apart into smaller particles as quickly as sugar cores during the coating process, resulting in multiparticulates with more uniform size distributions and less batch to batch variance. The melt-congeal cores are also smooth and round, making the cores easier to coat relative to sugar cores and the like.

Second, the melt-congeal cores can be formed into very small particles. Melt-congeal cores can be made with a volume weighted diameter of less than 100 microns. This allows multiparticulates to be formed at small size with a rapid dissolution rate. Moreover, the melt-congeal cores remain smooth and round even at small size, in contrast to small sugar cores which become increasingly irregular and difficult to coat as the size decreases.

Third, many of the materials used to form melt-congeal cores also tend to be hydrophobic. Thus, in contrast to water soluble core materials such as sugar, the cores will not absorb water. The release of the drug from the cores is therefore not affected by the core material. In addition, many of the materials used to form the core are biodegradable. Thus, the melt-congeal cores may be used in dosage forms in which non-biodegradable materials would not be appropriate, such as parenteral dosage forms.

Finally, the melt-congeal cores allow incorporation of other materials into the core that can be used to adjust the dissolution rate of the drug, or to alter the release rate of the drug from the multiparticulates. For example, the core may contain excipients such as swelling agents to rupture the core to increase dissolution of the drug. Alternatively, the matrix material may contain additional drug, or a different drug, to allow modification of the drug release profile. Such cores may release the drug quickly, or may provide slow release of the drug.

The foregoing and other objectives, features, and advantages of the invention will be more readily understood upon consideration of the following detailed description of the invention.

DETAILED DESCRIPTION OF PREFERRED EMBODIMENTS

Figure 1:
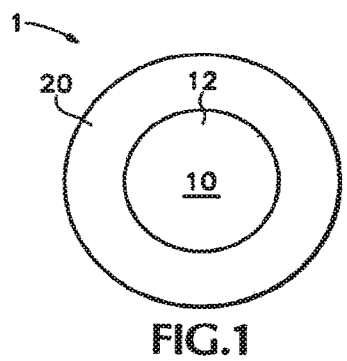
FIG. 1 is a cross-sectional schematic of a multiparticulate.

Referring to the drawings, there is shown in FIG. 1 a cross-sectional schematic of a multiparticulate 1 of the invention, comprising a melt-congeal core 10 comprising a matrix material 12 surrounded by a solid amorphous dispersion layer 20. The melt-congeal core may comprise other optional excipients or materials, such as a swelling agent, drug or a second drug, or dissolution enhancers. The solid amorphous dispersion layer comprises a drug and a polymer, in which at least a major portion of the drug is amorphous and dispersed in the polymer. The multiparticulates may also comprise an optional exterior coating surrounding the solid amorphous dispersion layer. The melt-congeal cores, solid amorphous dispersion layers, optional exterior coatings, and processes for forming the multiparticulates are described in more detail below.

Melt-Congeal Core

Matrix Materials

As shown in FIGS. 1-5, the melt-congeal core 10 comprises a matrix material 12. The matrix material serves two functions. First, the matrix material allows formation of relatively smooth, round cores that are amenable to coating. Second, the matrix material binds the optional excipients and/or drugs that may be incorporated into the core. The matrix material has the following physical properties: a sufficiently low viscosity in the molten state to form multiparticulates, as detailed below, and rapidly congeals to a solid when cooled below its melting point. For those multiparticulates incorporating drug in the core, the matrix preferably has a melting point below that of the melting point or decomposition point of the drug, and does not substantially dissolve the drug.

The melt-congeal cores consist essentially of a continuous phase of matrix material and optionally other excipients, with optional drug particles and optional swelling agent particles encapsulated within. Because of this, a sufficient amount of matrix material must be present to form smooth cores that are large enough to coat. In the case of cores containing solid particles, such as drug or swelling agent, the core must contain a sufficient amount of matrix material to encapsulate the drug and swelling agent to form relatively smooth and spherical cores, which are more easily coated by conventional spray-coating processes than irregularly-shaped ones. The matrix material may be present in the core from at least about 30 wt %, at least about 50 wt %, at least about 70 wt %, at least about 80 wt %, at least about 90 wt %, and up to 100 wt % based on the mass of the uncoated core.

In order to form small, smooth round cores, the matrix material must be capable of being melted and then atomized. The matrix material or mixture of materials is solid at 25° C. However, the matrix material melts, or is capable of melting with the addition of an optional processing aid, at a temperature of less than 200° C. so as to be suitable for melt-congeal processing described below. Preferably, the matrix material has a melting point between 50° C. and 150° C. Although the term "melt" generally refers to the transition of a crystalline material from its crystalline to its liquid state, which occurs at its melting point, and the term "molten" generally refers to such a crystalline material in its fluid state, as used herein, the terms are used more broadly. In the case of "melt," the term is used to refer to the heating of any material or mixture of materials sufficiently that it becomes fluid in the sense that it may be pumped or atomized in a manner similar to a crystalline material in the fluid state. Likewise "molten" refers to any material or mixture of materials that is in such a fluid state.

The matrix material is selected from the group consisting of waxes, long chain alcohols ($C_{12}$ or greater), fatty acid esters, glycolized fatty acid esters, phosphoglycerides, polyoxyethylene alkyl ethers, long chain carboxylic acids ($C_{12}$ or greater), sugar alcohols, and mixtures thereof. Exemplary matrix materials include highly purified forms of waxes, such as Carnauba wax, white and yellow beeswax, ceresin wax, microcrystalline wax, and paraffin wax; long-chain alcohols, such as stearyl alcohol, cetyl alcohol and polyethylene glycol; fatty acid esters (also known as fats or glycerides), such as isopropyl palmitate, isopropyl myristate, glyceryl monooleate, glyceryl monostearate, glyceryl palmitostearate, mixtures of mono-, di-, and trialkyl glycerides, including mixtures of glyceryl mono-, di-, and tribehenate, glyceryl tristearate, glyceryl tripalmitate and hydrogenated vegetable oils, including hydrogenated cottonseed oil; glycolized fatty acid esters, such as polyethylene glycol stearate and polyethylene glycol distearate; polyoxyethylene alkyl ethers; polyethoxylated castor oil derivatives; long-chain carboxylic acids such as stearic acid; and sugar alcohols such as mannitol and erythritol. The matrix material may comprise mixtures of materials, such as mixtures of any of the foregoing.

Preferably, the matrix material is selected from the group consisting of fatty acids esters, waxes, long-chain alcohols, ethoxylated fatty acid esters, long-chain carboxylic acids, and mixtures thereof.

Preferred fatty acid esters are glyceryl behenate and hydrogenated cottonseed oil.

Preferred waxes include microcrystalline wax, paraffin, ceresin wax and carnuaba wax.

Preferred long-chain alcohols include cetostearyl alcohol, stearyl alcohol and cetyl alcohol.

Preferred ethoxylated fatty acid esters include polyoxyl stearates and polyoxyl behenates.

In one embodiment, the matrix material is hydrophobic and poorly water soluble. Exemplary matrix materials that are hydrophobic include waxes and fatty acid esters.

Drug in Core

Figure 2:
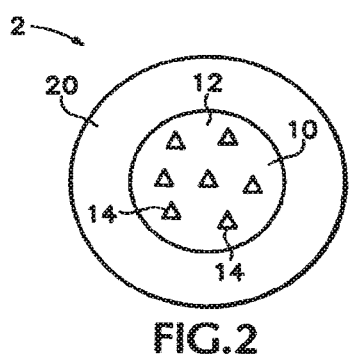
FIG. 2 is a cross-sectional schematic of another embodiment comprising drug in the core of the multiparticulate.

In another embodiment as illustrated in FIG. 2, the multiparticulate 2 comprises a core 10 containing a drug 14. The drug in its undispersed state may be either crystalline or amorphous. The core may contain drug in an amount of up to about 70 wt % based upon the total mass of the uncoated core. In one embodiment, the amount of drug in the core may range from 1 to 50 wt %, and more preferably from 5 to 40 wt %, and still more preferably from 10 to 30 wt % based on the mass of the uncoated core.

For drugs which are crystalline within the core, the drug in the core is preferably "substantially crystalline," meaning that at least 70 wt % of the drug is in the crystalline state. More preferably the drug is at least 80 wt % crystalline, and most preferably at least 90 wt %. In addition, the drug should have a low solubility in the molten matrix material. Dissolution of the drug in the matrix material can reduce the crystallinity of the drug in the finished core and compromise the drug's chemical and physical stability. The drug should have a solubility in the molten matrix material of less than about 30 wt %, more preferably less than about 20 wt %, and even more preferably less than about 10 wt %.

Alternatively, the drug in the core may be amorphous. The drug may either be present as pure amorphous drug, or may be present as particles of solid amorphous dispersion of drug in a matrix.

In those embodiments containing crystalline drug in the core, the matrix material should have a melting point below that of the melting point or decomposition point of the drug. By "decomposition point" of the drug is meant the temperature at which the drug decomposes. By selecting a matrix material that has a melt temperature below the melting point or decomposition point of the drug, a molten mixture may be formed at a temperature below that of the melting point of the drug. This allows the drug to remain in its native state while being formed into cores. For crystalline drugs, this means the drug remains in its original crystalline state without melting or changing to another crystalline form. Preferably, the matrix material becomes molten at a temperature that is 10° C. less than the melting point of the drug, more preferably at least 20° C. less than the melting point or decomposition point of the drug, and even more preferably at least 30° C. less than the melting point or decomposition point of the drug.

Swelling Agent

Figure 3:
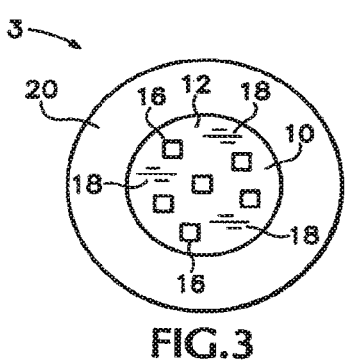
FIG. 3 is a cross-sectional schematic of another embodiment comprising a swelling agent in the core of the multiparticulate.

In another embodiment illustrated in FIG. 3, the multiparticulate 3 comprises a core 10 containing a water-swellable swelling agent 16 that expands upon contact with aqueous fluids. The swelling agent 16 is preferably present as a separate phase from the matrix material 12. The swelling agent may be present in an amount of from 1 to 40 wt %, more preferably from 5 to 35 wt %, and most preferably from 10 to 25 wt % based upon the mass of the uncoated core.

The first requirement of the swelling agent is that it is highly swelling. As the core imbibes water, the swelling agent must expand a sufficient amount to rupture the core. Preferably, the swelling agent, when contacted with aqueous gastric or simulated gastric fluid, can expand in volume such that its swelling ratio is at least about 2, more preferably at least about 3.5, and even more preferably at least about 5. The following in vitro test may be used to determine the "swelling ratio" of water swellable materials. The swelling agent is compressed into a compact using a 13/32-inch die, the compact having a strength ranging from 3 to 16 Kp/cm$^2$. The compact is then placed into a glass cylinder of approximately the same inside diameter as the compact and the volume of the compact is determined. Next, the glass cylinder is filled with simulated gastric buffer consisting of 0.01 M HCl and 0.12 M NaCl in deionized water. The glass cylinder and test media are all equilibrated at a constant temperature of 37° C. The volume of the compact is determined at several time intervals. The ratio of the volume of the compact after reaching a constant height to that of the volume of the dry compact is the swelling ratio, or swelling factor, of the swelling agent.

In addition, the swelling agent should swell rapidly. Rapid swelling is desired for two reasons. First, the multiparticulate should release the drug quickly. Therefore, swelling should be fast enough so that the core ruptures. Second, for multiparticulates comprising a water insoluble exterior coating 50 surrounding the drug layer 20 (as in FIG. 5), rapid swelling is often necessary to rupture the coating. If the swelling agent swells too slowly, the insoluble coating may slowly swell and expand rather than rupture. Alternatively, the components of the core may permeate through openings in the exterior coating, thus relieving the internal pressure within the core. Using the test described above, the rate at which swelling occurs may be determined. Preferably, the swelling agent reaches a swelling ratio of at least about 2 in the simulated gastric buffer within one hour, more preferably within about 30 minutes, and most preferably within about 15 minutes.

Finally, the swelling agent should also be such that it may be blended with the molten matrix material (described below) to form a flowable suspension. The swelling agent is preferably present as a separate phase in the core, so that when the core imbibes water, the swelling agent swells and ruptures the coating. Preferably, the swelling agent does not dissolve in the molten matrix, Thus, when the cores are formed using a melt method, the swelling agent remains as a solid suspended in the molten matrix. If the swelling agent does dissolve, it should phase separate into large domains of relatively pure swelling agent when the core congeals.

Exemplary swelling agents that are both highly swelling and swell rapidly include polymers such as sodium starch glycolate (commercially available as EXPLOTAB from Edward Mendell Co.), croscarmellose sodium (commercially available as AC-DI-SOL from FMC Corporation of Philadelphia, Pa.), and crospovidone. These polymers also are capable of remaining as a separate solid phase in a molten matrix.

Additional Core Excipients

The core may also contain a variety of other excipients, present in the core in an amount of from 0 to 40 wt %, based upon the mass of the uncoated core.

One preferred excipient is a dissolution enhancer, which may be used to increase the rate of water uptake by the core and consequent expansion of the swelling agent. The dissolution enhancer is a different material than the matrix material. The dissolution enhancer may be in a separate phase or a single phase with the matrix material. Preferably, at least a portion of the dissolution enhancer is phase-separated from the matrix material. As shown in FIG. 3, the optional dissolution-enhancer 18 is present as a separate phase in the matrix material 12. As water enters the core 10, the dissolution-enhancer dissolves, leaving channels which allow water to more rapidly enter the core to cause the swelling agent 16 to expand.

In general, dissolution enhancers are amphiphilic compounds and are generally more hydrophilic than the matrix materials. Examples of dissolution enhancers include: surfactants such as poloxamers, docusate salts, polyoxyethylene castor oil derivatives, polysorbates, sodium lauryl sulfate, and sorbitan monoesters; sugars, such as glucose, xylitol, sorbitol and maltitol; salts, such as sodium chloride, potassium chloride, lithium chloride, calcium chloride, magnesium chloride, sodium sulfate, potassium sulfate, sodium carbonate, magnesium sulfate and potassium phosphate; and amino acids, such as alanine and glycine; and mixtures thereof. A preferred surfactant-type dissolution-enhancer is a poloxamer (commercially available as the LUTROL or PLURONIC series from BASF Corp.).

The core may also contain other optional excipients, such as agents that inhibit or delay the release of drug from the multiparticulates. Such dissolution-inhibiting agents are generally hydrophobic and include dialkylphthalates such as dibutyl phthalate, and hydrocarbon waxes, such as microcrystalline wax and paraffin wax.

Another useful class of excipients comprises materials that may be used to adjust the viscosity of the molten feed used to form the cores. Such viscosity-adjusting excipients will generally make up 0 to 25 wt % of the core. The viscosity of the molten food is a key variable in obtaining cores with a narrow particle size distribution. For example, when a spinning-disk atomizer is employed, it is preferred that the viscosity of the molten mixture be at least about 1 cp and less than about 10,000 cp, more preferably at least 50 cp and less than about 1000 cp. If the molten mixture has a viscosity outside these preferred ranges, a viscosity-adjusting agent can be added to obtain a molten mixture within the preferred viscosity range. Examples of viscosity-reducing excipients include stearyl alcohol, cetyl alcohol, low molecular weight polyethylene glycol (i.e., less than about 1000 daltons), isopropyl alcohol, and water. Examples of viscosity-increasing excipients include microcrystalline wax, paraffin wax, synthetic wax, high molecular weight polyethylene glycols (i.e., greater than about 5000 daltons), ethyl cellulose, hydroxypropyl cellulose, hydroxypropyl methyl cellulose, methyl cellulose, silicon dioxide, microcrystalline cellulose, magnesium silicate, sugars, and salts.

For those embodiments containing a drug in the core, other excipients may be added to adjust the release characteristics of the drug from the cores. For example, an acid or base may be included in the composition to modify the rate at which drug is released in an aqueous use environment. Examples of acids or bases that can be included in the composition include citric acid, adipic acid, malic acid, succinic acid, tartaric acid, di- and tribasic sodium phosphate, di- and tribasic calcium phosphate, mono-, di-, and triethanolamine, sodium bicarbonate and sodium citrate dihydrate. Such excipients may make up 0 to 25 wt % of the core, based on the total mass of the core.

Still other excipients may be added to improve processing, such as excipients to reduce the static charge on the cores or to reduce the melting temperature of the matrix material Examples of such anti-static agents include talc and silicon dioxide. Flavorants, colorants, and other excipients may also be added in their usual amounts for their usual purposes. Such excipients may make up 0 to 25 wt % of the core, based on the total mass of the core.

In one embodiment, the uncoated melt-congeal core components are present in the following amounts, based upon the total mass of the uncoated core:
(i) matrix material from 80 to 100 wt %; and
(ii) optional excipients from 0 to 20 wt %.

In another embodiment, the uncoated core components are present in the following amounts, based upon the total mass of the uncoated core:
(i) matrix material from 30 to 90 wt %, more preferably 50 to 80 wt %;
(ii) drug up to 70 wt %, more preferably from 1 to 50 wt %, still more preferably from 5 to 40 wt %, and most preferably from 10 to 30 wt %; and
(ii) optional dissolution enhancer from 0 to 20 wt %, more preferably 2 to 15 wt %.

In another embodiment, the uncoated core components are present in the following amounts, based upon the total mass of the uncoated core:
(i) matrix material from 30 to 90 wt %, more preferably 50 to 80 wt %;
(ii) optional dissolution enhancer from 0 to 20 wt %, more preferably 2 to 15 wt %; and
(iii) swelling agent from 1 to 40 wt %, more preferably from 5 to 35 wt %, and most preferably from 10 to 25 wt %.

In another embodiment, the core contains the same drug as in the solid amorphous dispersion layer. The core provides slow release of the drug. The matrix material may be poorly water soluble, such as a wax or fat. Alternatively, the core may further comprise dissolution-inhibiting agents. Such an embodiment may provide immediate release of the drug from the solid amorphous dispersion layer, and controlled release of the drug from the core.

In another embodiment, the core contains the same drug as in the solid amorphous dispersion layer. The core provides fast release of the drug. The matrix material may be water soluble, such as a water soluble polymer or polyol. Alternatively, the core may further comprise dissolution-enhancing agents. Such an embodiment may provide immediate release of the drug from the solid amorphous dispersion layer, and relatively fast release of the drug from the core (albeit at a somewhat slower rate than dissolution of the drug from the solid amorphous dispersion layer).

In another embodiment, the core contains a second drug that is different than the drug in the solid amorphous dispersion layer. The core provides slow release of the second drug. The matrix material may be poorly water soluble, such as a wax or fat. Alternatively, the core may further comprise dissolution-inhibiting agents. Such an embodiment may provide immediate release of the drug from the solid amorphous dispersion layer, and controlled release of the second drug from the core.

In another embodiment, the core contains a second drug that is different than the drug in the solid amorphous dispersion layer. The core provides fast release of the second drug. The matrix material may be water soluble, such as a water soluble polymer or polyol. Alternatively, the core may further comprise dissolution-enhancing agents. Such an embodiment may provide immediate release of the drug from the solid amorphous dispersion layer, and relatively fast release of the second drug from the core.

Forming the Cores

The process used to form the cores comprises the steps of (a) forming a molten mixture comprising the matrix material and the other optional core components, (b) atomizing the molten mixture of step (a) to form droplets, and (c) congealing the droplets from step (b) to form cores. The steps of forming a molten mixture and atomizing may be performed sequentially or simultaneously.

The matrix material and other optional core components are combined to form a molten mixture. As previously noted, "molten mixture" refers to a mixture that is treated by heat, pressure or shear forces to the point that the mixture becomes sufficiently fluid that the mixture may be formed into droplets or atomized. Generally the mixture is molten in the sense that it will flow when subjected to one or more forces such as pressure, shear, and centrifugal force, such as that exerted by a centrifugal or spinning-disk atomizer. Thus, the mixture may be considered "molten" when the mixture, as a whole, is sufficiently fluid that it may be atomized.

For those embodiments in which the core contains a crystalline drug, the temperature of the molten mixture is maintained below that of the melting point or decomposition point of the drug but sufficiently high to form the molten mixture. In addition, the temperature of the molten matrix should be sufficiently low so that the solubility of the drug in the matrix material is less than 30 wt %.

Virtually any process may be used to form the molten mixture. A preferred method involves heating the matrix material in a tank until it is fluid and then adding the drug and swelling agent. Generally, the matrix material is heated to a temperature of about 10° C. or more above the temperature at which it becomes fluid. Alternatively, both the drug and the matrix material may be added to the tank and the mixture heated until the molten mixture has become fluid.

Once the molten mixture has become fluid and the drug has been added, the mixture is mixed to ensure that any optional drug or excipient added to the matrix material is substantially uniformly distributed therein.

An alternative method of forming the molten mixture is by an extruder. By "extruder" is meant a device or collection of devices that creates a molten extrudate by heat and/or shear forces and/or produces a uniformly mixed extrudate from a solid and/or liquid (e.g., molten) feed. Such devices include, but are not limited to single-screw extruders and twin-screw extruders, including co-rotating, counter-rotating, intermeshing, and non-intermeshing extruders. The molten mixture may optionally be directed to an accumulation tank, before being directed to a pump, which directs the molten mixture to an atomizer. Optionally, an in-line mixer may be used before or after the pump to ensure the molten mixture is substantially homogeneous. In each of these extruders the molten mixture is mixed to form a uniformly mixed extrudate. Such mixing may be accomplished by various mechanical and processing means, including mixing elements, kneading elements, and shear mixing by backflow. Thus, in such devices, the composition is fed to the extruder, which produces a molten mixture that can be directed to the atomizer.

In one embodiment, the composition is fed to the extruder in the form of a solid powder. The powdered feed can be prepared using methods well known in the art for obtaining powdered mixtures with high content uniformity. See *Remington's Pharmaceutical Sciences* (16th ed. 1980).

To aid in formation of the molten mixture, a processing aid may be added. Some matrix materials, such as sugar alcohols such as mannitol or erythritol, are capable of becoming molten at a temperature below their melting point in the presence of a processing aid such as water. The processing aid may act to depress the melting point of the matrix material, partially dissolve the matrix material, or both, thus allowing the matrix material to become molten. The processing aid may evaporate during formation of the melt-congeal cores, so that the resulting melt-congeal core contains only the matrix material but not the processing aid.

Once the molten mixture has been formed, it is delivered to an atomizer that breaks the molten mixture, or feed, into small droplets. Any suitable method can be used to deliver the molten mixture to the atomizer, including the use of pumps and various types of pneumatic devices such as pressurized vessels or piston pots. When an extruder is used to form the molten mixture, the extruder itself can be used to deliver the molten mixture to the atomizer. Typically, the molten mixture is maintained at an elevated temperature while delivering the mixture to the atomizer to prevent solidification of the mixture and to keep the molten mixture flowing.

Atomization may be conducted in a number of ways, including (1) by "pressure" or single-fluid nozzles; (2) by two-fluid nozzles; (3) by ultrasonic nozzles; (4) by mechanical vibrating nozzles; or (5) by centrifugal or spinning-disk atomizers. Detailed descriptions of atomization processes can be found in Lefebvre, *Atomization and Sprays* (1989) and in *Perry's Chemical Engineers' Handbook* (7th Ed. 1997), the disclosures of which are incorporated herein by reference.

A preferred method of atomizing is by centrifugal atomizers, also known as rotary atomizers or spinning-disk atomizers, whereby the molten mixture is fed onto a rotating surface, where it is caused to spread out by centrifugal force. The rotating surface may take several forms, examples of which include a flat disk, a cup, a vaned disk, and a slotted wheel. The surface of the disk may also be heated to aid in formation of the cores. Several mechanisms of atomization are observed with flat-disk and cup centrifugal atomizers, depending on the flow of molten mixture to the disk, the rotation speed of the disk, the diameter of the disk, the viscosity of the feed, and the surface tension and density of the feed. At low flow rates, the molten mixture spreads out across the surface of the disk and when it reaches the edge of the disk, forms a discrete droplet, which is then flung from the disk. As the flow of molten mixture to the disk increases, the mixture tends to leave the disk as a filament, rather than as a discrete droplet. The filament subsequently breaks up into droplets of fairly uniform size. At even higher flow rates, the molten mixture leaves the disk edge as a thin continuous sheet, which subsequently disintegrates into irregularly sized filaments and droplets. The diameter of the rotating surface generally ranges from 2 cm to 50 cm, and the rotation speeds range from 500 rpm to 10,000 rpm or higher, depending on the desired size of the cores.

Once the molten mixture has been atomized, the droplets are congealed, typically by contact with a gas or liquid at a temperature below the solidification temperature of the droplets. Typically, it is desirable that the droplets are congealed in less than about 60 seconds, preferably in less than about 10 seconds, more preferably in less than about 1 second. The congealing step often occurs in an enclosed space to simplify collection of the cores. In such cases, the temperature of the congealing media (either gas or liquid) will increase over time as the droplets are introduced into the enclosed space. Thus, a cooling gas or liquid is often circulated through the enclosed space to maintain a constant congealing temperature.

The cores are preferably made by a melt-congeal process comprising the steps of melting the matrix material and dispersing therein any optional components; and directing the so-formed melt to an atomizing apparatus, preferably a spinning disk atomizer operating at 1500 to 10,000 rpm, preferably 2500 to 6500 rpm, whereby small droplets of the melt are formed and radially dispersed by centrifugal force into a cooling chamber where they rapidly lose heat and congeal into small, generally spherical particles.

The resulting melt-congeal cores are generally smooth, round spheres. The cores may have a volume weighted mean diameter of from 10 microns up to 500 microns. Preferably, the volume weighted mean diameter of the cores is less than 250 microns, more preferably less than about 150 microns, and even more preferably less than 100 microns. In order to be amenable to coating, it is preferred that the melt-congeal cores have a volume-weighted mean diameter of at least about 20 microns. Such small melt-congeal cores provide faster dissolution of the drug relative to larger cores with the same drug loading. The inventors have found that the dissolution rate or release rate of the drug from the solid amorphous dispersion layer is primarily a function of the ratio of the surface area of the solid amorphous dispersion layer to the mass of the solid amorphous dispersion layer. Multiparticulates having a higher ratio of surface area to mass of the solid amorphous dispersion layer have faster dissolution rates. Thus, multiparticulates with smaller cores will have a faster dissolution rate relative to multiparticulates with larger cores at the same coating thickness of the solid amorphous dispersion layer. Alternatively, multiparticulates with smaller cores can have higher drug loadings (that is, the mass of drug per total mass of the multiparticulate) and still achieve the same dissolution rate as multiparticulates with larger cores at the same ratio of surface area to mass of the solid amorphous dispersion layer.

In addition, when such cores are incorporated into dosage forms that present the multiparticulates to the mouth, (such as a fast dissolving dosage form or a sachet), such small multiparticulates may be more pleasing to patients, since such small multiparticulates present a smooth, rather than gritty sensation in the mouth, if such multiparticulates are even felt at all.

Solid Amorphous Dispersion Layer

The solid amorphous dispersion layer 20 surrounds the core 10 and comprises a drug and a polymer. By "solid amorphous dispersion" is meant a material that is solid at 25° C. in which at least a portion of the drug is in the amorphous form and dispersed in the polymer.

"Amorphous" refers to material that is not crystalline. It has been found that for poorly water soluble drugs having poor bioavailability that bioavailability improves as the fraction of drug present in the amorphous state in the solid amorphous dispersion layer increases. Preferably, at least a major portion of the drug in the solid amorphous dispersion layer is amorphous. As used herein, the term "a major portion" of the drug means that at least about 60% of the drug in the solid amorphous dispersion layer is in the amorphous form, as opposed to the crystalline form; in other words, the amount of drug in crystalline form does not exceed about 40 wt %. Preferably the drug in the solid amorphous dispersion layer is "substantially amorphous," meaning that at least about 75 wt % of the drug in the solid amorphous dispersion layer is amorphous; in other words, the amount of drug in crystalline form does not exceed about 25 wt %. Even more preferably, the drug in the solid amorphous dispersion layer is "almost completely amorphous," meaning that at least about 90 wt % of the drug in the dispersion is amorphous; in other words, the amount of drug in the crystalline form does not exceed about 10 wt %. Amounts of crystalline drug may be measured by Powder X-Ray Diffraction (PXRD), by Scanning Electron Microscope (SEM) analysis, by Differential Scanning calorimetry (DSC), or by any other known quantitative measurement.

The amorphous drug can exist as a pure phase, as a solid solution of drug homogeneously distributed throughout the polymer or any combination of these states or those states that lie between them. Preferably, at least a portion of the drug and polymer are present in the form of a solid solution or molecular dispersion. The solid amorphous dispersion is preferably "substantially homogeneous" so that the amorphous drug is dispersed at the molecular level as homogeneously as possible throughout the polymer. As used herein, "substantially homogeneous" means that the drug present in relatively pure amorphous domains within the solid amorphous dispersion layer is relatively small, on the order of less than about 20 wt %, and preferably less than about 10 wt % of the total amount of drug in the solid amorphous dispersion layer. Solid amorphous dispersion layers of the present invention that are substantially homogeneous generally are more physically stable and have improved concentration-enhancing properties and, in turn improved bioavailability, relative to nonhomogeneous dispersions.

When the drug and the polymer have glass transition temperatures that differ by more than about 20° C., the fraction of drug present in relatively pure amorphous drug domains or regions within the solid amorphous dispersion layer can be determined by measuring the glass transition temperature ($T_g$) of the dispersion. $T_g$ as used herein is the characteristic temperature at which a glassy material, upon gradual heating, undergoes a relatively rapid (i.e., in 10 to 100 seconds) physical change from a glassy state to a rubbery state. The $T_g$ of an amorphous material such as a polymer, drug, or solid amorphous dispersion can be measured by several techniques, including by a dynamic mechanical analyzer (DMA), a dilatometer, a dielectric analyzer, and by DSC. The exact values measured by each technique can vary somewhat, but usually fall within 10° to 30° C. of each other. When the solid amorphous dispersion exhibits a single $T_g$, the amount of drug in pure amorphous drug domains or regions in the dispersion is generally less than about 10 wt %, confirming that the dispersion is substantially homogeneous and is a solid solution. This is in contrast to a simple physical mixture of pure amorphous drug particles and pure amorphous polymer particles, which generally display two distinct $T_g$s, one being that of the drug and the other that of the polymer. For a solid amorphous dispersion that exhibits two distinct $T_g$s, it may be concluded that at least a portion of the drug is present in relatively pure amorphous domains. Preferably, the solid amorphous dispersion displays at least one $T_g$ intermediate between that of pure amorphous drug and pure polymer, indicating that at least a portion of the drug and polymer are present as a solid solution of drug molecularly dispersed in the polymer. With DSC, the amount of drug present in relatively pure amorphous drug domains or regions may be determined by first measuring the $T_g$ of a substantially homogeneous dispersion with a known drug loading, to be used as a calibration standard. From such calibration data, the fraction of drug in relatively pure amorphous drug domains or regions can be determined. Alternatively, the amount of drug present in relatively pure amorphous drug domains or regions may be determined by comparing the magnitude of the heat capacity (1) that correlates to the drug's $T_g$ with (2) that which correlates to the $T_g$ of a physical mixture of amorphous drug and polymer.

The term "polymer" is used conventionally, meaning a compound that is made of monomers connected together to form a larger molecule. The polymer should be inert, in the sense that it does not chemically react with the drug in an adverse manner, and should be pharmaceutically acceptable. The polymer can be neutral or ionizable, and preferably has an aqueous-solubility of at least about 0.1 mg/mL over at least a portion of the pH range of about 1-8. Polymers suitable for use with the present invention may be cellulosic or non-cellulosic. Of these, ionizable and cellulosic polymers are preferred, with ionizable cellulosic polymers being more preferred. By "cellulosic" is meant a cellulose polymer that has been modified by reaction of at least a portion of the hydroxyl groups on the saccharide repeating units with a compound to form an ester or an ether substituent.

A preferred class of polymers comprises polymers that are "amphiphilic" in nature, meaning that the polymer has hydrophobic and hydrophilic portions. The hydrophobic portion may comprise groups such as aliphatic or aromatic hydrocarbon groups. The hydrophilic portion may comprise either ionizable or non-ionizable groups that are capable of hydrogen bonding such as hydroxyls, carboxylic acids, esters, amines or amides.

Polymers suitable for forming solid amorphous dispersions include polyvinylpyrollidone, polyoxyethylene-polyoxypropylene block copolymers (sold under the trade names PLURONIC and LUTROL), polyacrylates and polymethacrylates sold under the trade name EUDRAGIT, and ester and ether substituted cellulosic polymers. One preferred class of polymers is neutral, amphiphilic polymers such as hydroxypropyl methyl cellulose (HPMC) and hydroxypropyl methyl cellulose acetate.

A most preferred class of cellulosic polymers comprises polymers that are at least partially ionizable at physiologically relevant pH and include at least one ionizable substituent, which may be either ether-linked or ester-linked, Exemplary cellulosic polymers that are at least partially ionized at physiologically relevant pHs include: hydroxypropyl methyl cellulose acetate succinate, hydroxypropyl methyl cellulose succinate, hydroxypropyl cellulose acetate succinate, hydroxypropyl methyl cellulose phthalate, carboxyethyl cellulose, carboxymethyl cellulose, carboxymethylethyl cellulose, cellulose acetate phthalate, methyl cellulose acetate phthalate, hydroxypropyl methyl cellulose acetate phthalate, cellulose acetate trimellitate, and hydroxypropyl methyl cellulose acetate trimellitate.

A preferred subset of cellulosic ionizable polymers includes hydroxypropyl methyl cellulose acetate succinate (HPMCAS), cellulose acetate phthalate, cellulose acetate trimellitate, and carboxymethyl ethyl cellulose (CMEC). Most preferred is HPMCAS.

Additional polymers suitable for use in the solid amorphous dispersion layer are disclosed in US published patent application 2002/0103225, herein incorporated by reference.

The solid amorphous dispersion layer provides fast dissolution of the drug, or improves the concentration of dissolved drug in a use environment relative to a control composition consisting essentially of the drug alone without any polymer. As used herein, a "use environment" can be either the in vivo environment of the GI tract, subdermal, intranasal, buccal, intrathecal, ocular, intraaural, subcutaneous spaces, vaginal tract, arterial and venous blood vessels, pulmonary tract or intramuscular tissue of an animal, such as a mammal and particularly a human, or the in vitro environment of a test solution, such as Phosphate Buffered Saline (PBS) solution or a Model Fasted Duodenal (MFD) solution. Concentration enhancement may be determined through either in vitro dissolution tests or through in vivo tests. It has been determined that enhanced drug concentration in in vitro dissolution tests in MFD solution or PBS solution is a good indicator of in vivo performance and bioavailability. An appropriate PBS solution is an aqueous solution comprising 20 mM sodium phosphate ($Na_2HPO_4$), 47 mM potassium phosphate ($KH_2PO_4$), 87 mM NaCl, and 0.2 mM KCl, adjusted to pH 6.5 with NaOH. An appropriate MFD solution is the same PBS solution wherein there is also present 7.3 mM sodium taurocholic acid and 1.4 mM of 1-paimitoyl-2-oleyl-sn-glycero-3-phosphocholine. In particular, a composition of the present invention may be dissolution-tested by adding it to MFD or PBS solution and agitating to promote dissolution, or by performing a membrane permeation test as generally described in this section and described in detail in the Examples.

Preferably, when dosed to an aqueous use environment, a composition of the present invention provides a maximum drug concentration (MDC) that is at least 1.25-fold the MDC provided by a control composition, e.g., if the MDC provided by the control composition is 100 then a composition of the present invention comprising a solid amorphous dispersion of the drug provides an MDC of at least 125 μg/mL. The control composition is conventionally the undispersed drug alone such as the crystalline drug alone in its most thermodynamically stable crystalline form; in cases where a crystalline form of the drug is unknown, the control may be amorphous drug alone. The control composition may also be the drug plus an inert diluent that does not solubilize the drug. More preferably, the MDC achieved with the compositions of the present invention are at least 2-fold that of the control composition, even more preferably at least 3-fold, and most preferably at least 5-fold. Rather surprisingly, the compositions may achieve extremely large enhancements in aqueous concentration. In some cases, the MDC of very hydrophobic drugs provided by the compositions of the present invention are at least 10-fold, at least 50-fold, at least 200-fold, at least 500-fold, to more than 1000-fold that of the control composition.

Alternatively, the compositions of the present invention provide in an aqueous use environment a concentration versus time Area Under the Curve (AUC), for any period of at least 90 minutes between the time of introduction into the use environment and about 270 minutes following introduction to the use environment that is at least 1.25-fold that of the control composition, More preferably, the AUC in the aqueous use environment achieved with the compositions of the present invention are at least 2-fold, more preferably at least 3-fold, and most preferably at least 5-fold that of the control composition. For some hydrophobic drugs, the compositions may provide an AUC value that is at least 10-fold, at least 25-fold, at least 100-fold, and even more than 250-fold that of the control composition.

Alternatively, the compositions of the present invention, when dosed orally to a human or other animal, provide an AUC in drug concentration in the blood plasma or serum (or relative bioavailability) that is at least 1.25-fold that observed in comparison to the control composition. Preferably, the blood AUC is at least about 2-fold, more preferably at least about 3-fold, even more preferably at least about 4-fold, still more preferably at least about 6-fold, yet more preferably at least about 10-fold, and most preferably at least about 20-fold that of the control composition.

Alternatively, the compositions of the present invention, when dosed orally to a human or other animal, provide a maximum drug concentration in the blood plasma or serum ($C_{max}$) that is at least 1.25-fold that observed in comparison to the control composition. Preferably, the $C_{max}$ is at least about 2-fold, more preferably at least about 3-fold, even more preferably at least about 4-fold, still more preferably at least about 6-fold, yet more preferably at least about 10-fold, and most preferably at least about 20-fold that of the control composition. Thus, compositions that meet the in vitro or in vivo performance criteria, or both, are considered to be within the scope of the invention.

A typical in vitro test to evaluate enhanced drug concentration can be conducted by (1) administering with agitation a test composition (the multiparticulates) to a test medium; (2) in a separate test, adding an appropriate amount of control composition (crystalline drug) to an equivalent amount of test medium; and (3) determining whether the measured MDC and/or AUC of the test composition in the test medium is at least 1.25-fold that provided by the control composition. In conducting such a dissolution test, the amount of test composition and control composition used is that amount which, if all the drug had dissolved, would yield a drug concentration of at least 2-fold, more preferably at least 10-fold, and most preferably at least 100-fold that of the aqueous solubility or equilibrium concentration of the drug. For some test compositions of a very poorly water soluble drug, it may be necessary to administer an even greater amount of the test composition to determine the MDC.

MDC and/or AUC are typically determined by measuring the concentration of dissolved drug as a function of time by sampling the test medium and plotting drug concentration in the test medium against time. The MDC is taken to be the maximum value of dissolved drug measured over the duration of the test. The aqueous AUC is calculated by integrating the concentration versus time curve over any 90-minute time period between the time of introduction of the composition into the aqueous use environment (when time equals zero) and 270 minutes following introduction to the use environment (when time equals 270 minutes). Typically, when the composition reaches its MDC rapidly, in say less than about 30 minutes, the time interval used to calculate AUC is from time equals zero to time equals 90 minutes. However, if the AUC of a composition over any 90-minute time period described above meets these criteria, then the composition is considered to be within the scope of the invention.

To avoid drug particulates that would give an erroneous determination, the test solution is either filtered or centrifuged. "Dissolved drug" is typically taken as that material that either passes a 0.45 μm syringe filter or, alternatively, the material that remains in the supernatant following centrifugation. Filtration can be conducted using a 13 mm, 0.45 μm polyvinylidine difluoride syringe filter sold by Scientific Resources under the trademark TITAN®. Centrifugation is typically carried out in a polypropylene microcentrifuge tube by centrifuging at 13,000 G for 60 seconds. Other similar filtration or centrifugation methods can be employed and useful results obtained. For example, the use of other types of microfilters may yield values somewhat higher or lower (±10-40%) than that obtained with the filter specified above, but will still allow identification of preferred dispersions. It is recognized that this definition of "dissolved drug" encompasses not only monomeric solvated drug molecules but also a wide range of species such as polymer/drug assemblies that have submicron dimensions such as drug aggregates, aggregates of mixtures of polymer and drug, micelles, polymeric micelles, colloidal particles or nanocrystals, polymer/drug complexes, and other such drug-containing species that are present in the filtrate or supernatant in the dissolution test.

An in vitro membrane permeation test may also be used to evaluate the compositions of the present invention. Further details of this membrane permeation test are presented in commonly assigned U.S. Patent Application Ser. No. 60/557,897, entitled "Method and Device for Evaluation of Pharmaceutical Compositions," filed Mar. 30, 2004, the disclosure of which is incorporated herein by reference.

In general terms, a typical in vitro membrane permeation test to evaluate enhanced drug concentration can be conducted by providing a drug-permeable membrane between feed and permeate reservoirs, as described in detail in the Examples, then (1) administering a sufficient quantity of test composition (that is, the multiparticulates) to a feed test medium, such that if all of the drug dissolved, the theoretical concentration of drug would exceed the equilibrium concentration of the drug by a factor of at least 2; (2) separately adding an equivalent amount of control composition to an equivalent amount of feed test medium; (3) measuring the flux of drug across the membrane from the feed to the permeate reservoir; and (4) determining whether the measured maximum flux of drug provided by the test composition is at least 1.25-fold that provided by the control composition. A composition of the invention provides concentration enhancement if, when administered to an aqueous use environment, it provides a maximum flux of drug in the above test that is at least about 1.25-fold the maximum flux provided by the control composition. Preferably, the maximum flux provided by the compositions of the invention are at least about 1,5-fold, more preferably at least about 2-fold, and most preferably at least about 3-fold that provided by the control composition.

Relative bioavailability or $C_{max}$ of drugs in the compositions of the invention can be tested in vivo in animals or humans using conventional methods for making such a determination, such as a crossover study. In an exemplary in vivo crossover study, a test composition comprising the multiparticulates is dosed to half a group of test subjects and, after an appropriate washout period (e.g., one week) the same subjects are dosed with a control composition that consists of an equivalent quantity of crystalline drug as was dosed with the test composition, but with no dispersion polymer present. The other half of the group is dosed with the control composition first, followed by the test composition. Relative bioavailability is measured as the concentration of drug in the blood (serum or plasma) versus time AUC determined for the test group divided by the AUC in the blood provided by the control composition. Preferably, this test/control ratio is determined for each subject, and then the ratios are averaged over all subjects in the study. In vivo determinations of AUC and $C_{max}$ can be made by plotting the serum or plasma concentration of drug along the ordinate (y-axis) against time along the abscissa (x-axis). To facilitate dosing, a dosing vehicle may be used to administer the dose. The dosing vehicle is preferably water, but may also contain materials for suspending the test or control composition, provided these materials do not dissolve the composition or change the aqueous solubility of the drug in vivo. The determination of AUCs is a well-known procedure and is described, for example, in Welling, "Pharmacokinetics Processes and Mathematics," ACS Monograph 185 (1986).

Process for Forming the Spray Coated Dispersion Layer

The solid amorphous dispersion layer is formed by spray-coating a spray solution of solvent, dissolved drug and dissolved polymer onto the cores under conditions that result in rapid evaporation of the solvent to yield a solid amorphous dispersion layer surrounding the core. The spray solution is atomized into droplets. The fluidized cores are repeatedly circulated through the droplets. The drying conditions are such that the solvent in the droplets rapidly evaporates so as to form the solid amorphous dispersion layer.

The spray solution comprises the drug and polymer dissolved in a common solvent. Solvents suitable for spray-coating can be any compound or mixture of compounds in which the drug and the polymer are mutually soluble. Preferably, the solvent is also volatile with a boiling point of 150° C. or less. In addition, the solvent should have relatively low toxicity and be removed from the solid amorphous dispersion to a level that is acceptable according to The International Committee on Harmonization (ICH) guidelines. Removal of solvent to this level may require a subsequent processing step such as tray-drying. Exemplary solvents include methanol, ethanol, isopropyl alcohol, acetone, ethyl acetate, acetonitrile, methylene chloride, toluene, 1,1,1-trichloroethane, and tetrahydrofuran. Lower volatility solvents such as dimethyl acetamide or dimethylsulfoxide can also be used in small amounts in mixtures with a volatile solvent. Mixtures of solvents, such as 50% methanol and 50% acetone, can also be used, as can mixtures with water, so long as the polymer and drug are sufficiently soluble to make the spray-coating process practicable. Preferred solvents are alcohols, acetone, and mixtures thereof.

The amount of drug and polymer in the spray solution depends on the solubility of each in the spray solution and the desired ratio of drug to polymer in the resulting solid amorphous dispersion layer. Preferably, the spray solution comprises at least about 0.01 wt %, more preferably at least about 0.1 wt %, even more preferably at least about 1 wt %, and most preferably at least about 10 wt % dissolved solids.

The spray solution is sprayed onto the cores under conditions that cause the solvent to evaporate rapidly. The strong driving force for solvent evaporation is generally provided by maintaining the partial pressure of solvent in the spray-coating apparatus well below the vapor pressure of the solvent at the temperature of the drying droplets. This is accomplished by mixing the liquid droplets with a warm drying gas. In addition, at least a portion of the heat required for evaporation of solvent may be provided by heating the spray solution, or by heating the atomizing gas.

Generally, the spray solution temperature can range anywhere from just above the solvents freezing point to about 20° C. above its ambient pressure boiling point (by pressurizing the solution) and in some cases even higher. Spray solution flow rates to the spray nozzle can vary over a wide range depending on the type of nozzle, fluidized bed size and spray-coating conditions.

Generally, the energy for evaporation of solvent from the spray solution in a spray-coating process comes primarily from a drying gas, which is typically the fluidizing gas. The drying gas can, in principle, be essentially any gas such as air. For safety reasons and to minimize undesirable chemical interactions with the drug or other materials in the solid amorphous dispersion, an inert gas such as nitrogen, nitrogen-enriched air or argon may be utilized. The drying gas is typically introduced into the coating chamber at a temperature between about 20° and about 80° C. and preferably between about 30° and about 70° C. In general, the drying gas is maintained at a temperature sufficiently low that the cores will not melt during the spray-coating process. Accordingly, the inlet temperature is usually maintained at a temperature of at least 10° C. less than the melt temperature of the core. The atomizing gas temperature may range from 0 to 80° C. Preferably, the temperature in the coating chamber is controlled so that the cores do not exceed 50° C.

The large surface-to-volume ratio of the spray solution droplets after they impact the cores and the large driving force for evaporation of solvent leads to rapid solidification times for the droplets after they impact the cores. Droplet sizes may be less than 100 μm, less than 50 μm, or less than 20 μm. Solidification times should be less than about 20 seconds, preferably less than about 10 seconds, and more preferably less than 1 second. This rapid solidification is often critical to maintaining a uniform, homogeneous solid amorphous dispersion layer instead of separating into drug-rich and polymer-rich phases. As noted above, to obtain large enhancements in concentration and bioavailability it is often necessary to obtain as homogeneous a dispersion as possible.

The atomizer may be any suitable atomizer, such as a two fluid or three fluid nozzle. While the atomizer may be located at the bottom of the spray-coating apparatus as described above, the atomizer may alternatively be placed in the top or side walls of the spraying chamber and the chamber can be provided with more than one atomizer. It is however, preferred that the atomizer is provided in the bottom to obtain a more even and accurate distribution of the spray solution on the cores. Atomizing pressure is typically 1 to 3 bar.

Exemplary devices suitable for spray-coating include the Glatt Wurster coater, the Niro precision coater, and those disclosed in WO 02138126 A2, EP 0 741 603 B1 (Aeromatic-Fielder AG), and WO 00/40339 (Aeromatic-Fielder AG), Spray-coating processes and equipment are described generally in *Perry's Chemical Engineers' Handbook*, pages 20-54 to 20-57 (6th Ed. 1984).

In a preferred process for forming the solid amorphous dispersion layer, a Würster fluidized bed system is used. In this system, a cylindrical partition (the Würster column) is placed inside a conical product container in the spray-coating apparatus. A fluidizing gas passes through a distribution plate located at the bottom of the product container to fluidize the cores, with the majority of the upward moving gas passing through the Würster column. An atomizer (such as a nozzle) located at the bottom of the Wurster column atomizes the solution into droplets that travel upward. The droplets deposit on the cores entering the Wurster column as they pass through the droplets. The solvent in the droplets evaporates as the cores travel up the Wurster column and out into the drying chamber. The partially coated cores fall down outside of the Wurster column, where they are fluidized until passing through the Wurster column again. After repeatedly passing through the Wurster column, the cores are coated with a layer of solid amorphous dispersion of the drug and polymer.

To reduce static charges in order to apply a uniform coating, humidification of the fluidizing gas is helpful. The dew point is preferably greater than 15° C., and preferably ranges from 15° C. to 30° C., more preferably from 25° C. to 25° C. The fluidizing gas flow rate is typically 20-60 SCFM. Other process variables such as design of air distribution plate and Würster column height can be adjusted to optimize the quality of the fluidization and minimize agglomeration.

Spray-coating continues until a predetermined particle size or weight is obtained. The determination of the desired particle size or weight can be conducted in accordance with known classification procedures. Alternatively a predetermined amount of cores is sprayed with a predetermined amount of solution to produce the particles with the desired particle size or weight.

Following coating, the multiparticulates may stay in the spray-coating apparatus while fluidized for up to several minutes, further evaporating solvent from the multiparticulates. The final solvent content of the multiparticulates should be low, since this reduces the mobility of the drug in the solid amorphous dispersion layer, thereby improving its stability. Generally, the solvent content of the solid amorphous dispersion layer after spray-coating should be less than about 10 wt % and preferably less than about 2 wt %.

Following spray-coating, the multiparticulates can be dried to remove residual solvent from the solid amorphous dispersion layer using suitable drying processes, such as tray drying, vacuum drying, fluid bed drying, microwave drying, belt drying, rotary drying, and other drying processes known in the art. Preferred secondary drying methods include vacuum drying, or tray drying under ambient conditions. To minimize chemical degradation during drying, drying may take place under an inert gas such as nitrogen, or may take place under vacuum.

The average diameter of the multiparticulates after applying the solid amorphous dispersion layer may range from 20 microns to 3 mm. In a preferred embodiment, the multiparticulates have an average diameter of from 30 to 500 microns, more preferably from 40 to 200 microns.

The amount of drug in the multiparticulates depends on the desired dose of the drug, the amount of other excipients in the solid amorphous dispersion layer, and the mass of the cores. Typically, the coating weight of the solid amorphous dispersion layer ranges from less than 1 wt % to 90 wt % of the multiparticulate (100*(wt coating/(wt coating+wt core)). In general, the coating weight of the solid amorphous dispersion layer in the multiparticulates ranges from about 10 wt % to 60 wt %.

The thickness of the solid amorphous dispersion layer will depend on the amount of drug in the multiparticulate, the amount of polymer and other excipients in the solid amorphous dispersion layer, and the core weight. In general, the solid amorphous dispersion layer ranges from about 10 microns to about 150 microns in thickness. Smaller cores are capable of achieving a thinner solid amorphous dispersion layer at the same drug loading. For example, for a multiparticulate with a 250 micron diameter core, a 25 wt % coating ((wt coating/(wt coating wt core)*100) results in a solid amorphous dispersion layer thickness of about 14 microns, while a multiparticulate with a 1 mm diameter core with the same coating weight results in a solid amorphous dispersion layer thickness of about 54 microns. In one embodiment, the solid amorphous dispersion layer may be less than 30 microns, less than 25 microns, less than 20 microns, or even less than 15 microns thick.

The Drug

The drug in the drug layer 20 is a "poorly water soluble drug," meaning that the drug has an aqueous solubility of less than about 10 mg/mL at pH 6-7. The drug may have an even lower aqueous solubility, such as less than about 5 mg/mL, less than about 1 mg/mL, less than about 0.5 mg/mL, less than about 0.1 mg/mL, and even less than about 0.05 mg/mL. A useful measure of the solubility of poorly water soluble drugs is a dose-to-aqueous solubility ratio, which may be calculated by dividing the dose (in mg) by the aqueous solubility (in mg/mL). In general, it may be said that drugs useful in the invention have a dose-to-aqueous solubility ratio greater than about 10 mL, and more typically greater than about 100 mL, where the aqueous solubility in mg/mL is the minimum value observed in an aqueous solution at pH 6-7, and the dose is in mg.

Preferred classes of drugs include, but are not limited to, antihypertensives, antianxiety agents, anticlotting agents, anticonvulsants, blood glucose-lowering agents, decongestants, antihistamines, antitussives, antineoplastics, beta blockers, anti-inflammatories, antipsychotic agents, cognitive enhancers, cholesterol-reducing agents, triglyceride-reducing agents, anti-atherosclerotic agents, antiobesity agents, autoimmune disorder agents, anti-impotence agents, antibacterial and antifungal agents, hypnotic agents, anti-Parkinsonism agents, anti-Alzheimer's disease agents, antibiotics, anti-depressants, antiviral agents, glycogen phosphorylase inhibitors, and cholesteryl ester transfer protein inhibitors.

Each named drug should be understood to include any pharmaceutically acceptable forms of the drug. By "pharmaceutically acceptable forms" is meant any pharmaceutically acceptable derivative or variation, including stereoisomers, stereoisomer mixtures, enantiomers, solvates, hydrates, isomorphs, polymorphs, pseudomorphs, neutral forms, salt forms and prodrugs. Specific examples of poorly water soluble drugs suitable for use in the present invention include acyclovir, amlodipine, apomorphine, atorvastatin, celecoxib, chlorthalidone, clarithromycin, digitoxin, digoxin, erythromycin, famotidine, fluconazole, glipizide, griseofulvin, lidocaine, nadolol, nelfinavir, nifedipine, paroxetine, phenobarbital, prednisolone, sertraline, sildenafil, spironolactone, testosterone, thiabendazole, torcetrapib, valdecoxib, voriconazole, and ziprasidone.

The optional drug which may be incorporated into the core is not limited, and may be the same or different than the drug in the drug layer 20. The drug in the core may be a poorly water soluble drug.

Exterior Coating

Figure 4:
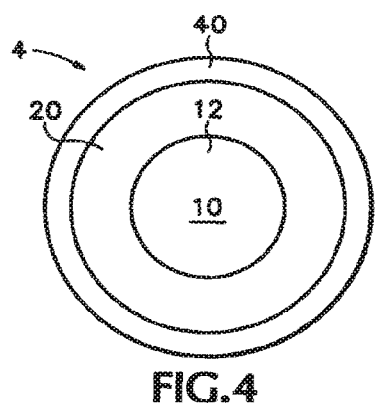
FIG. 4 is a cross-sectional schematic of another embodiment comprising a coating surrounding the exterior of the multiparticulate.

Following spray-coating of the solid amorphous dispersion layer, the multiparticulates may optionally be coated with an additional exterior coating. FIG. 4 is a cross-sectional schematic of another alternative embodiment comprising a multiparticulate 4 having an exterior coating 40 surrounding the solid amorphous dispersion layer 20. The exterior coating 40 may be any conventional coating, such as a protective film coating, a coating to provide delayed or sustained release of the drug from the solid amorphous dispersion layer 20, or to provide tastemasking. The exterior coating is applied under conditions that minimize changes to the solid amorphous dispersion layer.

In one embodiment, the coating 40 is an enteric coating to provide delayed release of the drug. By "enteric coating" is meant an acid resistant coating that remains intact and does not dissolve at pH of less than about 4. The enteric coating surrounds the multiparticulate so that the solid amorphous dispersion layer does not dissolve or erode in the stomach. The enteric coating may include an enteric coating polymer. Enteric coating polymers are generally polyacids having a $pK_a$ of about 3 to 5. Examples of enteric coating polymers include: cellulose derivatives, such as cellulose acetate phthalate, cellulose acetate trimellitate, hydroxypropyl methyl cellulose acetate succinate, cellulose acetate succinate, carboxy methyl ethyl cellulose, methylcellulose phthalate, and ethylhydroxy cellulose phthalate; vinyl polymers, such as polyvinyl acetate phthalate, vinyl acetate-maleic anhydride copolymer; polyacrylates; and polymethacrylates such as methyl acrylate-methacrylic acid copolymer, methacrylate-methacrylic acid-octyl acrylate copolymer, and styrene-maleic mono-ester copolymer. These may be used either alone or in combination, or together with other polymers than those mentioned above.

One class of preferred enteric coating materials are the pharmaceutically acceptable methacrylic acid copolymer which are copolymers, anionic in character, based on methacrylic acid and methyl methacrylate. Some of these polymers are known and sold as enteric polymers, for example having a solubility in aqueous media at pH 5.5 and above, such as the commercially available EUDRAGIT enteric polymers, such as Eudragit L 30, a polymer synthesized from dimethylaminoethyl methacrylate and Eudragit S. One preferred enteric coating solution consists of about 40 wt % Eudragit L30-D55 and 2.5 wt % triethylcitrate in about 57.5 wt % water.

Figure 5:
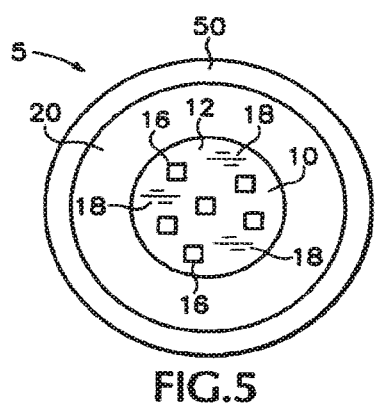
FIG. 5 is a cross-sectional schematic of another embodiment comprising a swelling agent in the core of the multiparticulate and surrounded by an exterior coating.

FIG. 5 is a cross-sectional schematic of another embodiment comprising a swelling agent 18 in the core 10 of the multiparticulate 5 and surrounded by an exterior coating 50 that is a water permeable, drug-impermeable exterior coating. The multiparticulate delivers drug by imbibing water through the coating 50. The core 10 may also include an optional dissolution enhancer 18 distributed throughout the matrix material 12. When placed in an aqueous fluid-containing environment such as a mouth or gastric environment, the multiparticulate permits aqueous fluid to pass through the coating 50 into the core 10. The imbibed aqueous fluid comes into contact with swelling agent 16, causing the same to swell and eventually cause rupture of the coating 50. In addition, the optional dissolution enhancer dissolves and leaves the core, leaving behind pores or channels that allow rapid diffusion of water into the core to increase the rate of water uptake by the swelling agent.

When the exterior coating 50 is used to provide taste-masking, the coating and core constituents are chosen so that the rupture is sufficiently delayed in time, for most or all of the multiparticulates, so that the coating ruptures in the stomach of a patient, rather than in the mouth. Multiparticulate rupture times may vary from about 1 to about 30 minutes, with substantially all of the multiparticulates in a given dose ruptured within one hour. In this fashion, virtually all of the drug is released well after the multiparticulates have passed through the mouth.

The coating 50 preferably comprises a water-permeable, substantially drug-impermeable polymer capable of permitting imbibition of aqueous fluid in a mouth or gastric environment Given the high surface to volume ratio of the small multiparticulates, the coatings may have relatively low water permeability and still be appropriate. This is particularly true when long lag times prior to rupture are desired. The coating has a low drug permeability to minimize drug release into the mouth or buccal use environment when the coating is intact. An important property of the coating is that it has sufficiently low ductility and tensile strength that it ruptures when the core swells rather than merely expanding with the core. Thus, preferred materials are those which produce coatings with elongation at break in the range of 10 to 30%. Materials with elongation at break values greater than about 30% often will only stretch when the core expands, rather than rupture. For many polymers, the proper molecular weight is a key property. If molecular weight is too high, the polymer may form a coating that is too strong or too elastic to rupture. For example, low-density polyethylene is likely too elastic and strong; however, a lower molecular weight form, such as some microcrystalline waxes, may be weak enough that they easily rupture. Also, morphology is an important property, Coatings can be weakened by making them semi-porous or grainy such that there is poor bonding between adjacent polymer domains. Addition of incompatible additives can also weaken the coating, allowing rupture. The coating should not be highly porous, or else the swelling pressure may be relieved or drug may escape prior to rupture. An additional property of the coating when used with compressed dosage forms such as chewable tablets is that it is sufficiently strong and ductile to resist damage during compaction.

In order to provide taste masking, coating materials should either be substantially water-insoluble, meaning a solubility in water at ambient temperature of less than 0.1 mg/ml, or should have sufficiently slow dissolution in water so that the coating ruptures prior to dissolution of a significant portion of the coating. Preferred water-insoluble coatings include: cellulose ethers such as ethyl cellulose; cellulose esters such as cellule acetate, cellulose acetate butyrate, cellulose triacetate, and cellulose acetate propionate; polyacrylates; and polymethacrylates. A particularly preferred cellulose ether is ethyl cellulose (commercially available as SURELEASE from Colorcon of West Point, Pa.). A particularly preferred polymethyaylate is a 2:1 copolymer of ethyl acrylate and methyl methacrylate (commercially available as EUDRAGIT NE from Rohm Pharma of Darmstadt, Germany). An exemplary coating solution using Eudragit NE30D contains 12.5% poly (ethyl acrylate, methyl methacrylate), 10% talc, and 77.5% water. The composition of the final dry coating (water removed) is 55% poly (ethyl acrylate, methyl methacrylate), and 45% talc.

Exterior coatings may include conventional plasticizers, including dibutyl phthalate; dibutyl sebacate; diethyl phthalate; dimethyl phthalate; triethyl citrate; benzyl benzoate; butyl and glycol esters of fatty acids; mineral oil; oleic acid; stearic acid; cetyl alcohol; stearyl alcohol; castor oil; corn oil; coconut oil; and camphor oil; and other excipients such as anti-tack agents, glidants, etc. For plasticizers, triethyl citrate, coconut oil and dibutyl sebacate are particularly preferred.

Exterior coatings can be formed using solvent-based and hot-melt coating processes. In solvent-based processes, the coating is made by first forming a solution or suspension comprising the solvent, the coating material and optional coating additives. The coating materials may be completely dissolved in the coating solvent, or only dispersed in the solvent as an emulsion or suspension or a combination of the two. Latex dispersions are an example of an emulsion or suspension that may be useful as in a solvent-based coating process. In one aspect, the solvent is a liquid at room temperature.

Coating may be conducted by conventional techniques, such as by pan coaters, rotary granulators and fluidized bed coaters such as top-spray, tangential-spray or bottom-spray (Würster coating), most preferably the latter.

A top-spray method can also be used to apply the coating. In this method, coating solution is sprayed down onto the fluidized cores. The solvent evaporates from the coated cores and the coated cores are re-fluidized in the apparatus. Coating continues until the desired coating thickness is achieved.

The coating may also be applied using a hot-melt coating technique. In this method, the coating excipients and additives are first melted and then sprayed onto the cores. Typically, the hot-melt coating is applied in a fluidized bed equipped with a top-spray arrangement.

Another method for applying a hot-melt coating to the cores is to use a modified melt-congeal method. In this method, the cores are suspended in the molten coating excipients, the melting point of the cores being greater than the melting point of the coating excipients. This suspension is then formed into droplets comprising the cores surrounded by the coating excipients. The droplets are typically formed by an atomizer, such as a rotary or spinning-disk atomizer. The droplets are then cooled to congeal the coating, forming the coated multiparticulates.

The exterior coating is present in a sufficient amount to slow or delay the release of drug. The exterior coating may range in an amount of from 5 to 60 wt % of the mass of the multiparticulates (100*(wt exterior coating/wt multiparticulate)).

Dosage Forms

The multiparticulates may be administered using any known dosage form. Exemplary oral dosage forms include: powders or granules; tablets; chewable tablets; capsules; unit dose packets, sometimes referred to in the art as "sachets" or "oral powders for constitution" (OPC); syrups; and suspensions. When the dosage form is an OPC, syrup, suspension or the like, in which the multiparticulate is suspended in a liquid when administered to the patient, the dosage form is administered to the patient sufficiently quickly so that the multiparticulates do not prematurely release the dosage form or the patient's mouth.

Conventional formulation excipients may be employed in the compositions of this invention, including those excipients well-known in the art. Generally, excipients such as fillers, disintegrating agents, pigments, binders, lubricants, glidants, flavorants, and so forth may be used for customary purposes and in typical amounts without adversely affecting the properties of the compositions. These excipients may be utilized after the multiparticulate compositions have been formed, in order to formulate the compositions into tablets, capsules, suspensions, powders for suspension, and the like.

Examples of tastemasking agents include sweeteners such as aspartame, compressible sugar, dextrates, lactose, mannitol, maltose, sodium saccharin, sorbitol, and xylitol, and flavors such as banana, cherry, *eucalyptus* oil, menthol, orange, peppermint oil, raspberry, strawberry, watermelon, and wild cherry.

Examples of dosage form excipients, fillers, or diluents include lactose, mannitol, xylitol, dextrose, sucrose, sorbitol, compressible sugar, microcrystalline cellulose, powdered cellulose, starch, pregelatinized starch, dextrates, dextran, dextrin, dextrose, maltodextrin, calcium carbonate, dibasic calcium phosphate, tribasic calcium phosphate, calcium sulfate, magnesium carbonate, magnesium oxide, poloxamers such as polyethylene oxide, and hydroxypropyl methyl cellulose.

Examples of surface active agents include sodium lauryl sulfate and polysorbate 80.

Examples of disintegrants include sodium starch glycolate, sodium carboxymethyl cellulose, calcium carboxymethyl cellulose, croscarmeliose sodium, crospovidone (polyvinylpolypyrrolidone), methyl cellulose, microcrystalline cellulose, powdered cellulose, starch, pregelatinized starch, and sodium alginate.

Examples of tablet binders include acacia, alginic acid, carbomer, carboxymethyl cellulose sodium, dextrin, ethylcellulose, gelatin, guar gum, hydrogenated vegetable oil, hydroxyethyl cellulose, hydroxypropyl cellulose, hydroxypropyl methyl cellulose, methyl cellulose, liquid glucose, maltodextrin, polymethacrylates, povidone, pregelatinized starch, sodium alginate, starch, sucrose, tragacanth, and zein.

Examples of lubricants include calcium stearate, glyceryl monostearate, glyceryl palmitostearate, hydrogenated vegetable oil, light mineral oil, magnesium stearate, mineral oil, polyethylene glycol, sodium benzoate, sodium lauryl sulfate, sodium stearyl fumarate, stearic acid, talc, and zinc stearate.

Examples of glidants include silicon dioxide, talc and cornstarch.

One preferred dosage form is a capsule that may be filled with the multiparticulates.

Chewable tablets for oral administration are another preferred dosage form. Such a dosage form may be formed by combining the multiparticulates with compressible sugar, a filler such as microcrystalline cellulose, a disintegrant, and flavorants. To reduce the risk of breaking the coating of the multiparticulates, soft excipients or excipients with small particle sizes may be used. These ingredients may be mixed together followed by addition of a lubricant such as magnesium stearate, followed by further mixing, followed by compression.

Without further elaboration, it is believed that one of ordinary skill in the art can, using the foregoing description, utilize the present invention to its fullest extent. Therefore, the following specific embodiments are to be construed as merely illustrative and not restrictive of the scope of the invention. Those of ordinary skill in the art will understand that variations of the conditions and processes of the following examples can be used.

EXAMPLES

Attrition Comparison

This example demonstrates that melt-congeal cores experience less attrition during the spray-coating process than sucrose cores.

First, melt-congeal cores comprising 100 wt % gylercyl behenate (COMPRITOL 888®, a mixture of glycerol mono-, di- and tri-behenates, available from Gatte Fosse, Paramus, N.J.) were prepared as follows. The COMPRITOL was delivered to a B&P 27-mm twin-screw extruder at a rate of 250 g/min. The extruder temperature was maintained at about 93° C. The material was then pumped using a 2.4 cc Zenith gear pump (located inside a 95° C. hot box) to the center of a 4-inch diameter spinning-disk atomizer to form multiparticulates. The surface of the spinning disk atomizer was maintained at 90° C. while making the multiparticulates, and the disk was rotating at 3000 rpm. The particles formed by the spinning-disk atomizer were congealed in ambient air and collected. The cores were sieved to obtain a fraction with a size range of 180-250 µm.

Sucrose cores (6080 sugar spheres, NF, available from Paulaur Corp., Cranbury, N.J.) were sieved to obtain a fraction with a size range of 180-250 µm.

To compare core attrition during the spray-coating process, the melt-congeal cores and sucrose cores were each separately evaluated by placing samples of each in a fluid bed coater operated at typical spray-coating conditions. For these tests, a 100 g sample of each respective sample was placed in a Mini-Glatt fluid bed coater with a Wurster column. The inlet temperature was 30° C., atomizing air pressure was 2 bar (nozzle used without coating solution), and fluidizing gas flow rate was 26.4 cfm. Samples of the coated cores were withdrawn from a sample port at regular 15 minute intervals. Samples were evaluated using optical microscopy. The percent attrition observed (weight of particles <180 µm) is shown in Table 1. After 60 minutes, the melt-congeal cores showed 12.5 wt % attrition, while the sucrose cores showed 50 wt % attrition.

TABLE 1

| Time (min) | Attrition (wt %) | |
|---|---|---|
| | Melt-Congeal Cores | Sucrose Cores |
| 0 | 0 | 0 |
| 15 | 2 | 6 |
| 30 | 3 | 20 |
| 60 | 12.5 | 50 |

Examples 1-3

These examples disclose multiparticulates of the embodiment of FIG. 1 comprising melt-congeal cores and solid amorphous dispersion layers. The inventors found that by decreasing the dispersion coating and maintaining a constant melt-congeal core size, the increasing ratio of surface area to coating mass results in increasing drug release rate.

First, melt-congeal cores comprising 100 wt % COMPRITOL 888® were prepared as follows. The COMPRITOL was added to a sealed, jacketed stainless-steel tank. Heating fluid at 90° C. was circulated through the jacket of the tank, and the COMPRITOL was melted and stirred. The COMPRITOL feed solution was pumped at a rate of about 100 g/min using a Zenith gear pump to the center of a 4-inch diameter spinning-disk atomizer rotating at 10,000 rpm, the surface of which was heated to 90° C. The particles formed by the atomizer were congealed in ambient air and collected. The cores were sieved to obtain a fraction with a size range of 63-75 µm.

Next, a solid amorphous dispersion containing 50 wt % celecoxib and 50 wt % HPMCAS (AQOAT-MG from Shin Etsu, Tokyo, Japan) was coated onto the melt congeal cores as follows. A solution was formed containing 158.9 g celecoxib (5 wt %), 158.9 g HPMCAS (5 wt %), 2701.0 g acetone (85 wt %), and 158.9 g water (5 wt %). The solution was sprayed onto 120 g of the melt congeal cores in a Mini-Glatt fluid bed coater with a Wurster column. The spray solution was pumped into the fluid bed coater at a rate of 3.5 g/min. The inlet temperature was 35° C., atomizing air pressure was 2 bar, and fluidizing gas flow rate was 22.5 cfm. The solid amorphous dispersion layer was applied until a coating weight of 23.2 wt % was achieved (coating wt/coating plus core wt). 58.3 g of the so-coated cores were removed from the fluid bed coater, and set aside as the multiparticulates for Example 1. A sample of the coated cores of Example 1 was observed by SEM analysis and the approximate average diameter was about 90 µm. The surface area per gram of coating was $25 \times 10^4$ mm$^2$/g.

The multiparticulates remaining in the fluid bed coater were further coated, until a coating weight for the solid amorphous dispersion layer of 52.4 wt % was achieved. 61.3 g of coated cores were removed from the fluid bed coater, and set aside as the multiparticulates of Example 2. The approximate average size of the dispersion-coated cores as determined by SEM analysis was about 130 μm. The surface area per coating weight was $9.4 \times 10^4$ mm²/g.

An additional sample of 90.2 g coated cores was removed from the fluid bed coater after a coating weight for the solid amorphous dispersion layer of 75.0 wt % was achieved. Finally, after a solid amorphous dispersion layer of 87.1 wt % was achieved, 186.5 g of coated cores were removed from the fluid bed coater, and set aside as the multiparticulates of Example 3. The approximate average size of the dispersion-coated cores as determined by SEM analysis was about 230 μm. The surface area per gram of coating was $4.1 \times 10^4$ mm²/g.

Celecoxib Release from Multiparticulates of Examples 1-3

The rate of release of celecoxib in vitro from multiparticulates of Examples 1-3 was determined using the follow procedure. A sample of the multiparticulates were placed into a USP Type 2 dissoette flask equipped with Teflon-coated paddles rotating at 100 rpm. A sufficient amount of the multiparticulates was added to provide about 400 mg of celecoxib. The flask contained 900 mL of simulated mouth buffer ($KH_2PO_4$ buffer, pH 7.3, with 0.5 wt % polysorbate 80 (sold as Tween 80, available commercially from ICI)) at 37.0±0.5° C. Samples were taken using a syringe attached to a cannula with a 70 μm filter. A sample of the fluid in the flask was drawn into the syringe, the cannula was removed, and a 0.45-μm filter was attached to the syringe. One mL of sample was filtered into a High Performance Liquid Chromatography (HPLC) vial. Samples were collected at 0, 5, 10, 20, 30, 60, 90, and 120 minutes following addition of the multiparticulates to the flask. The samples were analyzed using HPLC (Zorbax S6-C8 column, 3.5 μm particles, 7.5 cm×4.6 mm 45/55 5 mM triethanolamine, pH 7.0/acetonitrile at 1.5 mL/min; absorbance measured at 254 nm with a diode array spectrophotometer).

The amount of drug released was calculated based on the potency assay of the formulation. To measure the potency of the multiparticulates, about 2 mg of the multiparticulates were weighed and added to a 10 mL volumetric flask. Next, about 8 mL methanol was added, and the solution was sonicated for 20 minutes. The flask was cooled to room temperature and filled to volume with methanol. An aliquot of the solution was then centrifuged for 5 minutes at 13,000 rpm, and analyzed to determine the total amount of drug in the formulation. The potency assay of the formulation was used to calculate the amount of drug added for each dissolution test. The amount of drug in each sample was divided by the total amount of drug added for the test, and the results are reported as percent of assay. The results of these dissolution tests are given in Table 2.

TABLE 2

| Time (min) | Celecoxib Released from multiparticulates of Example 1 (% assay) | Celecoxib Released from multiparticulates of Example 2 (% assay) | Celecoxib Released from multiparticulates of Example 3 (% assay) |
| --- | --- | --- | --- |
| 0 | 0 | 0 | 0 |
| 5 | 84 | 50 | 18 |
| 10 | 96 | 71 | 33 |
| 20 | 96 | 89 | 58 |
| 30 | 96 | 94 | 75 |
| 60 | 96 | 94 | 96 |
| 90 | 96 | 94 | 99 |
| 120 | 97 | 94 | 99 |

The results in Table 2 show that as the dispersion coating is decreased for a given core size, the surface area per coating weight increases, and drug release rate is increased. For Example 1, the surface area per gram of coating was $25 \times 10^4$ mm²/g, while the surface area per gram of coating for Examples 2 and 3 was $9.4 \times 10^4$ mm²/9 and $4.1 \times 10^4$ mm²/g respectively. Example 1 had the fastest release rate, followed by Examples 2 and 3 respectively.

Example 4

This example discloses a multiparticulate of the embodiment of FIG. 1 comprising a melt-congeal core and a solid amorphous dispersion layer. This example demonstrates that multiparticulates with small cores can achieve equivalent drug release rates with higher drug loading relative to multiparticulates made from larger cores made from sugar spheres.

First, melt-congeal cores were prepared as in Example 1. The cores were sieved to obtain a fraction with a size range of 63-75 μm.

Next, a solid amorphous dispersion containing 50 wt % celecoxib and 50 wt % HPMCAS-LG was coated onto the melt congeal cores as follows. A solution was formed containing 62.5 g celecoxib (5 wt %), 62.5 g HPMCAS (5 wt %), 1061.7 g methanol (85 wt %), and 62.5 g water (5 wt %). The solution was sprayed onto 120 g of the melt congeal cores in a Mini-Glatt fluid bed coater with a Wurster column, and aliquots of the coated cores were periodically removed. The spray solution was pumped into the fluid bed coater at a rate of 3 g/min. The inlet temperature was 36° C., atomizing air pressure was 2 bar, and fluidizing gas flow rate was 23 cfm. After 84.0 wt % dispersion had been added (dispersion wt/dispersion plus core wt), the spray solution flow was discontinued, and the dispersion-coated cores were dried for 2 minutes with the fluidizing gas, SEM analysis showed that the average size of the dispersion-coated cores was about 150 μm. The surface area per coating weight was $5.8 \times 10^4$ mm²/g. The drug loading was 42 wt %.

Control 2

The multiparticulates of Control 2 comprised a sucrose core and a solid amorphous dispersion layer.

Sucrose cores (SUGLETS®, NP Pharm, Bazainville, France) (sucrose and maize starch spheres) with an average size of about 125 μm were coated with a solid amorphous dispersion containing 50 wt % celecoxib and 50 wt % HPMCAS-LG as follows. A solution was formed containing 60 g celecoxib (5 wt %), 60 g HPMCAS (5 wt %), and 1078 g methanol (90 wt %). The solution was sprayed onto 80₉ of the cores in a Mini-Glatt fluid bed coater with a Wurster column. The spray solution was pumped into the fluid bed coater at a rate of 2-4 g/min. The inlet temperature was 33-35° C., atomizing air pressure was 2 bar, and fluidizing gas flow rate was 30® 32 cfm. After 54.1 wt % dispersion had been added (dispersion wt/dispersion plus core wt), the spray solution flow was discontinued, and the dispersion-coated cores were dried for 2 minutes with the fluidizing gas. Following coating, the multiparticulates were placed in a 40° C. convection oven overnight for additional drying. The average size of the dispersion-coated cores was about 195 µm by SEM. The surface area per coating weight was $5.4 \times 10^4$ mm$^2$/g. The drug loading was 27 wt %.

Control 3

The multiparticulates of Control 3 comprised a sucrose core and a solid amorphous dispersion layer.

Sucrose cores (Nu-Core™, available from Chr. Hansen, Inc., Milwaukee, Wis.) with an average size of about 300 µm were coated with a solid amorphous dispersion containing 50 wt % celecoxib and 50 wt % HPMCAS-LG as described above for Control 1. The spray solution contained celecoxib, HPMCAS, methanol, and water in a ratio of 5/5/85/5. The solution was sprayed onto the cores in a Mini-Glatt fluid bed coater with a Wurster column to obtain a coating weight of 22 wt % (dispersion wt/dispersion plus core wt). The average size of the dispersion-coated cores was about 350 µm by SEM. The surface area was $6.5 \times 10^4$ mm$^2$/g coating. The drug loading was 11 wt %.

The dispersion-coated cores were analyzed using powder x-ray diffraction (PXRD), and compared to crystalline celecoxib and sucrose cores alone. The crystalline peaks found in the dispersion-coated cores corresponded to the crystalline peaks found in the sucrose cores, and not to the crystalline peaks in the celecoxib alone, indicating that the celecoxib in the dispersion-coated cores was amorphous.

Celecoxib Release from Multiparticulates of Example 4

The rate of release of celecoxib in vitro from multiparticulates of Example 4, and the multiparticulates of Controls 2 and 3, was determined as described above. Results are shown below in Table 3.

TABLE 3

| Time (min) | Celecoxib Released from multiparticulates of Example 4 (% assay) | Celecoxib Released from multiparticulates of Control 2 (% assay) | Celecoxib Released from multiparticulates of Control 3 (% assay) |
|---|---|---|---|
| 0 | 0 | 0 | 0 |
| 5 | 44 | 13 | 36 |
| 10 | 72 | 22 | 52 |
| 20 | 90 | 60 | 86 |
| 30 | 91 | 84 | 91 |
| 60 | 93 | 100 | 92 |

The results in Table 3 show that the release rate of celecoxib from the multiparticulates of Example 4 was similar to that of Controls 2 and 3, with the multiparticulates of Example 4 releasing drug a little more rapidly than Controls 2 and 3. However, Example 4 had a significantly higher drug loading of 42 wt %, as compared with 27 wt % and 11 wt % for Controls 2 and 3 respectively. These results show that the smaller cores of the present invention allow a higher drug loading to be achieved for a given release rate compared with multiparticulates made from larger cores while still attaining release rates that are similar to those provided by multiparticulates with larger cores.

Example 5

This example discloses a multiparticulate of the embodiment of FIG. 5 comprising a melt-congeal core, a solid amorphous dispersion layer, and an exterior, coating.

First, melt-congeal cores comprising 60 wt % COMPRITOL 888® (the matrix material), 35.0 wt % croscarmellose sodium (ACDISOL from FMC of Philadelphia, Pa.)(swelling agent), and 5 wt % of poloxamer (PLURONIC F127 from BASF of Mount Olive, N.J.) (dissolution enhancer) were prepared using the following procedure. The COMPRITOL and the PLURONIC were added to a sealed, jacketed stainless-steel 1 L tank equipped with a mechanical mixing paddle. Heating fluid was circulated through the jacket of the tank. After about 14 minutes, the mixture had melted, having a temperature of about 93° C. The ACDISOL was added to the melt and mixed for 5 minutes, resulting in a molten feed. The molten feed was pumped using a gear pump (Zenith Pump, Parker Hannifin Corp, Model C-9000, 2.4 cc/rev) to the center of a 4-inch diameter spinning-disk atomizer, the surface of which was heated to 90° C. The disk was spinning at 5,000 rpm. The particles formed by the spinning-disk atomizer were congealed in ambient air and collected. A sample of the melt-congeal cores was observed by SEM analysis and the approximate average diameter of the melt-congeal cores was determined to be about 230 µm.

Next, a solid amorphous dispersion layer containing 25 wt % valdecoxib and 75 wt % HPMCAS (AQOAT-LG, available from Shin Etsu, Tokyo, Japan) was coated onto the melt congeal cores as follows. A spray solution was formed containing 7.5 g valdecoxib (2.5 wt %), 22.6 g HPMCAS (7.5 wt %), 256 g methanol (85 wt %), and 15 g water (5 wt %). The solution was sprayed onto 50 g of the melt congeal cores in a Mini-Glatt fluid bed coater with a Würster column. The spray solution was pumped into the fluid bed coater at a rate of 4.6 g/min. The inlet temperature was 33° C., atomizing air pressure was 2.2 bar, and fluidizing gas flow rate was 26 cfm. The humidity was controlled to eliminate static (with a dew point setting of 15° C.). After 33.1 wt % solid amorphous dispersion layer had been added (dispersion wt/dispersion plus core wt), the spray solution flow and humidification were discontinued, and the multiparticulates were dried for 5 minutes with the fluidizing gas.

The multiparticulates were then coated with an exterior coating as follows. A spray solution was prepared by diluting an aqueous ethylcellulose dispersion, SURELEASE E-7-7050 (available from Colorcon as an aqueous emulsion containing 25 wt % solids) to 15 wt % solids in water. The solution was sprayed onto 50 g of the dispersion-coated cores in a Mini-Glatt fluid bed coater with a Wurster column. The spray solution was pumped into the fluid bed coater at a rate of 3.6 g/min. The inlet temperature was 59° C., atomizing air pressure was 2.2 bar, and fluidizing gas flow rate was 25 cfm. After 22.7 wt % exterior coating had been added (dispersion wt/dispersion plus core wt), the spray solution flow was discontinued, and the coated multiparticulates were dried for 5 minutes with the fluidizing gas. SEM analysis showed that the diameter was about 310 µm.

Valdecoxib Release from Multiparticulates of Example 5

The rate of release of valdecoxib in vitro from multiparticulates of Example 5 was determined using the following procedure, About 220 mg of the multiparticulates of Example 5 were placed into a USP Type 2 dissoette flask equipped with Teflon-coated paddles rotating at 100 rpm. The flask contained 900 mL of simulated mouth buffer ($KH_2PO_4$ buffer, pH 7.3, with 0.5 wt % polysorbate 80 (sold as Tween™ 80, available commercially from ICI)) at 37.0±0.5° C. Samples were taken using a syringe attached to a cannula with a 70 µm filter. A sample of the fluid in the flask was drawn into the syringe, the cannula was removed, and a 0.45-µm filter was attached to the syringe, One mL of sample was filtered into a High Performance Liquid Chromatography (HPLC) vial. Samples were collected at 0, 1, 2, 3, 5, 10, 20, 30, and 60 minutes following addition of the multiparticulates to the flask. The samples were analyzed using HPLC (Zorbax SB-C8 column, 3.5 µm particles, 7.5 cm×4.6 mm i.d.; 55/45 5 mM triethanolamine, pH 7.0/acetonitrile at 1.5 mL/min; absorbance measured at 256 nm with a diode array spectrophotometer).

The amount of drug released was calculated based on the potency assay of the formulation. To measure the potency of the multiparticulates of Example 5, about 80 mg of the multiparticulates were weighed and added to a 25 mL volumetric flask. Next, about 10 mL acetonitrile/methanol (80/20 vol/vol) was added, and the solution was sonicated for 15 minutes. The flask was cooled to room temperature and filled to volume with acetonitrile/methanol (80/20 vol/vol). An aliquot of the solution was then centrifuged for 5 minutes at 13,000 rpm, and analyzed to determine the total amount of drug in the formulation. The potency assay of the formulation was used to calculate the amount of drug added for each dissolution test. The amount of drug in each sample was divided by the total amount of drug added for the test, and the results are reported as percent of assay. The results of these dissolution tests are given in Table 4.

TABLE 4

| Time (min) | Valdecoxib Released from multiparticulates of Example 5 (% assay) |
| --- | --- |
| 0 | 0 |
| 1 | 1 |
| 2 | 3 |
| 3 | 6 |
| 5 | 11 |
| 10 | 16 |
| 20 | 19 |
| 30 | 23 |
| 60 | 56 |

The results in Table 4 show release of valdecoxib from the multiparticulates, following an initial delay.

Examples 6-9

These examples disclose multiparticulates of the embodiment of FIG. 1 comprising melt-congeal cores and solid amorphous dispersion layers with a third drug, [2R,4S]4[(3,5-bis-trifluoromethyl-benzyl)-methoxycarbonyl-amino]-2-ethyl-6-trifluoromethyl-3,4-dihydro-2H-quinoline-1-carboxylic acid ethyl ester, also known as torcetrapib. For Examples 6-9, the dispersion coating weight was varied on melt-congeal cores of a constant size. The increasing ratio of surface area to coating mass (decreasing dispersion coating weight) resulted in increasing drug release rate.

First, melt-congeal cores were prepared as in Example 1. The cores were sieved to obtain a fraction with a size range of 75-106 µm.

Next, a solid amorphous dispersion containing 25 wt % torcetrapib and 75 wt % HPMCAS-MG was coated onto the melt congeal cores as follows. A solution was formed containing 3 wt % torcetrapib, 9 wt % HPMCAS, and 88 wt % acetone. The solution was sprayed onto 55 g of the melt congeal cores in a Mini-Glatt fluid bed coater with a Würster column. The spray solution was pumped into the fluid bed coater at a rate of 2.5 g/min. The inlet temperature was 33° C., atomizing air pressure was 2.2 bar, and fluidizing gas flow rate was 21.9 cfm. The solid amorphous dispersion layer was applied until a coating weight of about 10 wt % was achieved (coating wt/coating plus core wt). 8.4 g of the so-coated cores were removed from the fluid bed coater, and set aside as the multiparticulates for Example 6. The approximate average size of the dispersion-coated cores as determined by SEM analysis was about 90 µm. The surface area per gram of coating was $6.7×10^4$ mm$^2$/g.

The multiparticulates remaining in the fluid bed coater were further coated, until a coating weight for the solid amorphous dispersion layer of about 30 wt % was achieved. 8 g of coated cores were removed from the fluid bed coater, and set aside as the multiparticulates of Example 7. The approximate average size of the dispersion-coated cores as determined by SEM analysis was about 100 µm. The surface area per coating weight was $6.0×10^4$ mm$^2$/g.

The multiparticulates remaining in the fluid bed coater were further coated, until a coating weight for the solid amorphous dispersion layer of about 50 wt % was achieved. 38.2 g of coated cores were removed from the fluid bed coater, and set aside as the multiparticulates of Example 8. The volumetric mean particle size of a sample of the coated cores of Example 8 was determined using the Malvern Mastersizer 2000 particle size analyzer, and the average diameter was 109 µm. The surface area per coating weight was $5.5×10^4$ mm$^2$/g.

Finally, after a solid amorphous dispersion layer of about 75 wt % was achieved, all remaining coated cores were removed from the fluid bed coater, and set aside as the multiparticulates of Example 9. The volumetric mean particle size of a sample of the coated cores of Example 9 was determined using the Malvern particle size analyzer, and the average diameter was 138 µm. The surface area per coating weight was $4.3×10^4$ mm$^2$/g.

Control 4

The multiparticulates of Control 4 comprised a sucrose core and a solid amorphous dispersion layer.

Sucrose cores (3035, Paulaur Corp., Cranbury, N.J.) with an average size of about 600 µm were coated with a solid amorphous dispersion containing 25 wt % torcetrapib and 75 wt % HPMCAS-MG as described above. The solid amorphous dispersion layer was applied until a coating weight of about 10 wt % was achieved (coating wt/coating plus core wt). The volumetric mean particle size of a sample of the coated cores of Control 4 was determined using the Malvern particle size analyzer, and the average diameter was 649 µm. The surface area per coating weight was $0.92×10^4$ mm$^2$/g.

Torcetrapib Release from Multiparticulates of Examples 6-9

The rate of release of torcetrapib in vitro from multiparticulates of Examples 6-9, and Control 4, was determined using the follow procedure. A sample of the multiparticulates was placed into a USP Type 2 dissoette flask equipped with Teflon-coated paddles rotating at 100 rpm. A sufficient amount of the multiparticulates was added to provide about 100 µg/mL of torcetrapib. The flask contained buffer solution (6 mM $KH_2PO_4$, 30 mM NaCl, 60 mM KCl, pH 6.8, with 2 wt % polysorbate 80 (sold as Tween™ 80, available commercially from ICI)) at 37.0±0.5° C. Samples were taken using a syringe attached to a cannula with a 10 µm filter. A sample of the fluid in the flask was drawn into the syringe, the cannula was removed, and a 0.45-µm filter was attached to the syringe. One mL of sample was filtered into a High Performance Liquid Chromatography (HPLC) vial. Samples were collected at 0, 5, 10, and 20 minutes following addition of the multiparticulates to the flask. The samples were analyzed using HPLC (Waters Symmetry C8 column, 17/83 0.2% $H_3PO_4$/methanol, absorbance measured at 256 nm with a diode array spectrophotometer).

The amount of drug released was calculated based on the potency assay of the formulation. To measure the potency of the multiparticulates, a sufficient amount of the multiparticulates were weighed and added to a 10 mL volumetric flask to obtain approximately 100 µg/mL torcetrapib. Next, the flask was filled to volume with methanol, and stirred overnight. An aliquot of the solution was then filtered using a 0.45-µm filter, and analyzed to determine the total amount of drug in the formulation. The potency assay of the formulation was used to calculate the amount of drug added for each dissolution test. The amount of drug in each sample was divided by the total amount of drug added for the test, and the results are reported as percent of assay. The results of these dissolution tests are given in Tables 5 and 6.

TABLE 5

| Time (min) | Torcetrapib Released from multi-particulates of Example 6 (% assay) | Torcetrapib Released from multi-particulates of Example 7 (% assay) | Torcetrapib Released from multi-particulates of Example 8 (% assay) | Torcetrapib Released from multi-particulates of Example 9 (% assay) |
|---|---|---|---|---|
| 0 | 0 | 0 | 0 | 0 |
| 5 | 89 | 84 | 53 | 64 |
| 10 | 92 | 90 | 62 | 69 |
| 20 | 94 | 92 | 75 | 72 |

The results in Table 5 show generally that as the dispersion coating is increased for a given core size, the surface area per coating weight decreases, and initial drug release rate is decreased.

Table 6 shows the release rate achieved by Example 6 compared to Control 4.

TABLE 6

| Time (min) | Torcetrapib Released from multiparticulates of Example 6 (% assay) | Torcetrapib Released from multiparticulates of Control 4 (% assay) |
|---|---|---|
| 0 | 0 | 0 |
| 5 | 89 | 66 |
| 10 | 92 | 92 |
| 20 | 94 | 94 |

The results in Table 6 show that increasing core size with a constant coating weight decreases the surface area per coating weight, and initial drug release rate is decreased. For Example 6, the surface area per gram of coating was $6.7 \times 10^4$ $mm^2$/g, while the surface area per gram of coating for Control 4 was $0.92 \times 10^4$ $mm^2$/g. Example 6 showed faster initial drug release than Control 4.

The terms and expressions which have been employed in the foregoing specification are used therein as terms of description and not of limitation, and there is no intention in the use of such terms and expressions of excluding equivalents of the features shown and described or portions thereof, it being recognized that the scope of the invention is defined and limited only by the claims which follow.

The invention claimed is:

1. A pharmaceutical composition comprising multiparticulates, the multi particulates comprising:
    (a) a melt-congeal core comprising a matrix material present in an amount of at least 30 wt % of the core, the matrix material being solid at 25° C. and having a melt temperature of less than 200° C., wherein the matrix material is selected from the group consisting of waxes, long chain alcohols, fatty acid esters, glycolized fatty acid esters, phosphoglycerides, polyoxyethylene alkyl ethers, long chain carboxylic acids, sugar alcohols, and mixtures thereof; and
    (b) a solid amorphous dispersion layer coating the melt-congeal core, the solid amorphous dispersion layer comprising a drug and a polymer, wherein the matrix material and the polymer are not the same compound, wherein at least 75 wt % of the drug in the solid amorphous dispersion layer is amorphous and wherein at least a portion of the solid amorphous dispersion layer is in the form of a substantially homogeneous solid solution, and wherein the solid solution exhibits a single glass-transition temperature;

wherein the weight of the solid amorphous dispersion layer ranges from 1 wt % to 90 wt % of the multiparticulates.

2. The composition of claim 1 wherein the matrix material is present in the melt-congeal core in an amount of at least 80 wt % of the melt-congeal core.

3. The composition of claim 1 wherein the melt-congeal core further comprises a swelling agent.

4. The composition of claim 1 wherein the melt-congeal core further comprises the drug.

5. The composition of claim 1 wherein the melt-congeal core further comprises a second drug.

6. The composition of claim 1 wherein at least 90 wt % of the drug in the solid amorphous dispersion layer is amorphous.

7. The composition of claim 6 wherein the polymer is selected from the group consisting of polyvinylpyrrolidone, hydroxypropyl methyl cellulose, hydroxypropyl methyl cellulose acetate succinate, cellulose acetate phthalate, cellulose acetate trimellitate, and carboxymethyl ethyl cellulose.

8. The composition of claim 1 wherein the melt temperature is from 50° C. to 150° C.

9. The composition of claim 1 wherein the melt-congeal core has a volume weighted mean diameter of less than about 150 µm.

10. The composition of claim 1 wherein the multiparticulates have a volume weighted mean diameter of less than 300 µm.

11. The composition of claim 1 further comprising an exterior coating surrounding the solid amorphous dispersion layer, the exterior coating being formed of a material different from the solid amorphous dispersion layer material.

* * * * *